(12) United States Patent
Balasubramaniam

(10) Patent No.: US 7,994,119 B2
(45) Date of Patent: Aug. 9, 2011

(54) COMPOUNDS FOR CONTROL OF APPETITE

(75) Inventor: Ambikaipakan Balasubramaniam, Cincinnati, OH (US)

(73) Assignee: University Of Cincinnati, Cincinnati, OH (US)

( * ) Notice: Subject to any disclaimer, the term of this patent is extended or adjusted under 35 U.S.C. 154(b) by 1094 days.

(21) Appl. No.: 11/658,061

(22) PCT Filed: Jul. 19, 2005

(86) PCT No.: PCT/US2005/025407
§ 371 (c)(1), (2), (4) Date: Jan. 19, 2007

(87) PCT Pub. No.: WO2006/020207
PCT Pub. Date: Feb. 23, 2006

(65) Prior Publication Data
US 2008/0221038 A1 Sep. 11, 2008

Related U.S. Application Data

(60) Provisional application No. 60/589,199, filed on Jul. 19, 2004.

(51) Int. Cl.
*A61K 38/00* (2006.01)
*A61P 3/04* (2006.01)

(52) U.S. Cl. .......................... 514/4.8; 514/4.9

(58) Field of Classification Search .................. None
See application file for complete search history.

(56) References Cited

U.S. PATENT DOCUMENTS

| | | | | |
|---|---|---|---|---|
| 5,622,699 | A * | 4/1997 | Ruoslahti et al. | 506/9 |
| 6,962,902 | B2 * | 11/2005 | Balasubramanium et al. | 514/9 |
| 7,465,710 | B2 * | 12/2008 | Balasubramanium et al. | 514/18 |
| 2006/0009395 | A1 * | 1/2006 | Balasubramanium et al. | 514/18 |
| 2007/0197445 | A1 * | 8/2007 | Balasubramaniam | 514/14 |
| 2009/0227519 | A1 * | 9/2009 | Balasubramaniam | 514/17 |

OTHER PUBLICATIONS

Beechanahalli et al. Convenient high yield and stereoselective synthesis of O-glycopeptides using N-alpha-Fmoc-Tyr/Ser[Beta-D-Glc(OAc)4]OPfp generated in solution. Tetrahedron Letters 2004, 45, pp. 355-358.*
Parker et al. Neuropeptide Y receptors as targets for anti-obesity drug develpment: prespective and current status. European Journal of Pharmacology. 2002. vol. 440, pp. 173-187.*
H.J.C. Berendsen. A Glimpse of the Holy Grail? Science (1998) 282, pp. 642-643.*
Rudinger. In: Peptide Hormones, JA Parsons, Ed. (1976) 1-7.*
Sigma. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://www.neurosci.pharm.utoledo.edu/MBC3320/vasopressin.htm; 5 pages.*
D.E. Smilek, et al. Proc. Natl. Acad. Sci. USA (1991) 88, pp. 9633-9637.*
D. Voet and J.G. Voet. Biochemistry, 2nd Edition.(1995), pp. 235-241.*
Sandgren et al. Nuclear Targeting of Macromolecular Polyanions by an HIV-Tat Derived Peptide. The Journal of Biological Chemistry. 2002. vol. 277, No. 41, pp. 38877-38883.*
Kirby, D.A. et al., Neuropeptide Y: Y1 and Y2 Affinities of the Complete Series of Analogues with Single D-Residue Substitutions, J. Med. Chem., 1993, 36:3802-8.
Kirby, D.A. et al., Identification of High-Potency Neuropeptide Y Analogues through Systematic Lactamization, J. Med. Chem., 1997, 40:210-5.
Feinstein, R.D. et al., Structural Requirements for Neuropeptide Y18-36-Evoked Hypotension: A Systematic Study, J. Med. Chem., 1992, 35:2836-43.
Beck-Sickinger, A.G. et al., Complete L-alanine scan of neuropeptide Y reveals ligands binding to Y1 and Y2 receptors with distinguished conformations, Biochem., 1994, 225:947-58.
Cox, H.M. et al., Structure-activity relationships with neuropeptide Y analogues: a comparison of human Y1-, Y2- and rat Y2-like systems, Regul. Pept., 1998, 75-76:3-8.
Mullins, D. et al., Identification of Potent and Selective Neuropeptide Y Y1 Receptor Agonists with Orexigenic Activity in Vivo, Mol. Pharmacol., 2001, 60:534-40.

* cited by examiner

*Primary Examiner* — Marcela M Cordero Garcia
(74) *Attorney, Agent, or Firm* — Wood, Herron & Evans, LLP

(57) ABSTRACT

This invention relates generally to peptides including tripeptides and to methods for pharmaceutical treatment of mammals using such tripeptides and analogs thereof. More specifically, the invention is directed to neuropeptide Y ("NPY") receptor antagonists and agonists including O-glycosylated tripeptides, i.e. O-glycopeptides, and extended tripeptides, and their analogs, as well as to PYY analogs, to pharmaceutical compositions containing such tripeptides and PYY analogs, and to methods of treatment of mammals using such tripeptides and PYY analogs. In addition, the invention relates to methods of treatment of mammals using such tripeptides and PYY analogs for control of appetite, blood pressure, cardiovascular response, libido, and circadian rhythm.

11 Claims, 3 Drawing Sheets

SEQUENCE LISTING

```
<160> NUMBER OF SEQ ID NOS: 18

<210> SEQ ID NO 1
<211> LENGTH: 11
<212> TYPE: PRT
<213> ORGANISM: Human immunodeficiency virus

<400> SEQUENCE: 1

Tyr Gly Arg Lys Lys Arg Arg Gln Arg Arg Arg
1               5                   10

<210> SEQ ID NO 2
<211> LENGTH: 36
<212> TYPE: PRT
<213> ORGANISM: Homo sapiens
<220> FEATURE:
<221> NAME/KEY: MOD_RES
<222> LOCATION: (36)..(36)
<223> OTHER INFORMATION: AMIDATION

<400> SEQUENCE: 2

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 3
<211> LENGTH: 36
<212> TYPE: PRT
<213> ORGANISM: Porcine neuropeptide Y
<220> FEATURE:
<221> NAME/KEY: MOD_RES
<222> LOCATION: (36)..(36)
<223> OTHER INFORMATION: AMIDATION

<400> SEQUENCE: 3

Tyr Pro Ser Lys Pro Asp Asn Pro Gly Glu Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Tyr
        35

<210> SEQ ID NO 4
<211> LENGTH: 36
<212> TYPE: PRT
<213> ORGANISM: Porcine peptide YY
```

-continued

```
<400> SEQUENCE: 4

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
                20                  25                  30

Arg Gln Arg Tyr
            35

<210> SEQ ID NO 5
<211> LENGTH: 36
<212> TYPE: PRT
<213> ORGANISM: Homo sapiens

<400> SEQUENCE: 5

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
                20                  25                  30

Arg Gln Arg Tyr
            35

<210> SEQ ID NO 6
<211> LENGTH: 12
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 6

Arg His Tyr Leu Asn Trp Val Thr Arg Gln Arg Tyr
1               5                   10

<210> SEQ ID NO 7
<211> LENGTH: 12
<212> TYPE: PRT
<213> ORGANISM: Artificial
<220> FEATURE:
<223> OTHER INFORMATION: Artificial peptide
<220> FEATURE:
<221> NAME/KEY: MISC_FEATURE
<223> OTHER INFORMATION: reduced peptide bond between 11 and 12 (CH2NH)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 7

Arg His Trp Leu Asn Leu Val Thr Arg Gln Arg Tyr
1               5                   10

<210> SEQ ID NO 8
<211> LENGTH: 15
<212> TYPE: PRT
<213> ORGANISM: Artificial
<220> FEATURE:
<223> OTHER INFORMATION: Artficial peptide
```

```
<220> FEATURE:
<221> NAME/KEY: MISC_FEATURE
<223> OTHER INFORMATION: Reduced peptide bond between positions 14 and
      15 (CH2-NH)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (10)..(10)
<223> OTHER INFORMATION: Nva
<220> FEATURE:
<221> NAME/KEY: MOD_RES
<222> LOCATION: (15)..(15)
<223> OTHER INFORMATION: AMIDATION

<400> SEQUENCE: 8

Ala Ser Xaa Arg His Tyr Xaa Asn Trp Xaa Thr Arg Gln Arg Tyr
1               5                   10                  15

<210> SEQ ID NO 9
<211> LENGTH: 9
<212> TYPE: PRT
<213> ORGANISM: Artificial
<220> FEATURE:
<223> OTHER INFORMATION: Artificial peptide

<400> SEQUENCE: 9

Cys Leu Ser Ser Arg Leu Asp Ala Cys
1               5

<210> SEQ ID NO 10
<211> LENGTH: 11
<212> TYPE: PRT
<213> ORGANISM: Artificial
<220> FEATURE:
<223> OTHER INFORMATION: Artificial peptide

<400> SEQUENCE: 10

Arg Tyr Arg Gly Asp Leu Gly Leu Gly Arg Arg
1               5                   10

<210> SEQ ID NO 11
<211> LENGTH: 13
<212> TYPE: PRT
<213> ORGANISM: Artificial
<220> FEATURE:
<223> OTHER INFORMATION: Artificial peptide

<400> SEQUENCE: 11

Cys Arg Tyr Arg Gly Asp Leu Gly Leu Gly Arg Arg Cys
1               5                   10

<210> SEQ ID NO 12
<211> LENGTH: 15
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (12)..(12)
<223> OTHER INFORMATION: bAla
```

```
<220> FEATURE:
<221> NAME/KEY: MOD_RES
<222> LOCATION: (15)..(15)
<223> OTHER INFORMATION: AMIDATION

<400> SEQUENCE: 12

Tyr Gly Arg Lys Lys Arg Arg Gln Arg Arg Arg Xaa Trp Arg Tyr
1               5                   10                  15

<210> SEQ ID NO 13
<211> LENGTH: 18
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (12)..(12)
<223> OTHER INFORMATION: bAla
<220> FEATURE:
<221> NAME/KEY: MOD_RES
<222> LOCATION: (18)..(18)
<223> OTHER INFORMATION: AMIDATION

<400> SEQUENCE: 13

Tyr Gly Arg Lys Lys Arg Arg Gln Arg Arg Arg Xaa Trp Arg Tyr Trp
1               5                   10                  15

Arg Tyr

<210> SEQ ID NO 14
<211> LENGTH: 15
<212> TYPE: PRT
<213> ORGANISM: Artificial
<220> FEATURE:
<223> OTHER INFORMATION: Artificial peptide
<220> FEATURE:
<221> NAME/KEY: MISC_FEATURE
<222> LOCATION: (12)..(12)
<223> OTHER INFORMATION: Glycolic acid
<220> FEATURE:
<221> NAME/KEY: MOD_RES
<222> LOCATION: (15)..(15)
<223> OTHER INFORMATION: AMIDATION

<400> SEQUENCE: 14

Tyr Gly Arg Lys Lys Arg Arg Gln Arg Arg Xaa Trp Arg Tyr
1               5                   10                  15

<210> SEQ ID NO 15
<211> LENGTH: 5
<212> TYPE: PRT
<213> ORGANISM: Artificial
<220> FEATURE:
<223> OTHER INFORMATION: Artificial peptide
<220> FEATURE:
<221> NAME/KEY: CARBOHYD
<222> LOCATION: (1)..(1)
<223> OTHER INFORMATION: carbohydrate is B-D-glucose
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: AMIDATION

<400> SEQUENCE: 15

Tyr Xaa Trp Arg Tyr
1               5
```

```
<210> SEQ ID NO 16
<211> LENGTH: 13
<212> TYPE: PRT
<213> ORGANISM: Artificial
<220> FEATURE:
<223> OTHER INFORMATION: Artificial peptide
<220> FEATURE:
<221> NAME/KEY: MISC_FEATURE
<223> OTHER INFORMATION: Cys residues 1 and 9 are bonded (Cys--Cys)
<220> FEATURE:
<221> NAME/KEY: MOD_RES
<222> LOCATION: (10)..(10)
<223> OTHER INFORMATION: bAla
<220> FEATURE:
<221> NAME/KEY: MOD_RES
<222> LOCATION: (13)..(13)
<223> OTHER INFORMATION: AMIDATION

<400> SEQUENCE: 16

Cys Leu Ser Ser Arg Leu Asp Ala Cys Xaa Trp Arg Tyr
1               5                   10

<210> SEQ ID NO 17
<211> LENGTH: 15
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: bAla
<220> FEATURE:
<221> NAME/KEY: MOD_RES
<222> LOCATION: (15)..(15)
<223> OTHER INFORMATION: AMIDATION

<400> SEQUENCE: 17

Arg Tyr Arg Gly Asp Leu Gly Leu Gly Arg Arg Xaa Trp Arg Tyr
1               5                   10                  15

<210> SEQ ID NO 18
<211> LENGTH: 17
<212> TYPE: PRT
<213> ORGANISM: Artificial
<220> FEATURE:
<223> OTHER INFORMATION: Artificial peptide
<220> FEATURE:
<221> NAME/KEY: MISC_FEATURE
<223> OTHER INFORMATION: Cys residues 1 and 13 are bonded (Cys--Cys)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (14)..(14)
<223> OTHER INFORMATION: bala
<220> FEATURE:
<221> NAME/KEY: MOD_RES
<222> LOCATION: (17)..(17)
<223> OTHER INFORMATION: AMIDATION

<400> SEQUENCE: 18

Cys Arg Tyr Arg Gly Asp Leu Gly Leu Gly Arg Arg Cys Xaa Trp Arg
1               5                   10                  15

Tyr
```

COMPOUNDS FOR CONTROL OF APPETITE

CROSS-REFERENCE TO RELATED APPLICATIONS

This application claims the benefit of U.S. Provisional Application No. 60/589,199, filed on Jul. 19, 2004, the disclosure of which is hereby incorporated by reference herein in its entirety.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant/Contract No. 3R01 GM47122-0851 awarded by the National Institutes of Health.

BACKGROUND OF THE INVENTION

This invention relates generally to peptides including tripeptides, and to methods for pharmaceutical treatment of mammals using such peptides and analogs thereof. More specifically, the invention relates to O-glycosylated and extended tripeptides and their analogs, as well as to peptide YY (PYY) analogs, to pharmaceutical compositions containing such tripeptides and PYY analogs, and to methods of treatment of mammals using such tripeptides and PYY analogs. In addition, the invention relates to methods of treatment of mammals using such tripeptides and PYY analogs for control of appetite, blood pressure, cardiovascular response, libido, and circadian rhythm.

1. Appetite and Obesity

Obesity is a major disorder affecting as much as one third of the North American population. Several studies have shown that such individuals are at increased risk in developing cardiovascular disease (hypertension and hypercholesterolemia), diabetes and several types of cancer. The effective treatment of obesity, however, remains a largely unachieved goal. Existing pharmacotherapeutic approaches to weight loss involve the use of amphetamine-based agents such as amphetamine, diethylpropion, mazindol and fenfluramine which act directly on the CNS to lower food intake by modulating dopaminergic, adrenergic and/or serotonergic mechanisms. Although weight loss can be achieved with such agents, their use is restricted due to CNS side-effects, potential addiction liability and the production of tolerance to their actions, with chronic administration leading to potential depression, vestibular disturbances, hallucinations and addiction, as well as interference with the actions other drugs such as MAO inhibitors and antihypertensives. There is also a subpopulation of obese patients that is refractory to present anorectic drug treatments. The medical need is high for an effective anorectic agent which overcomes the above disadvantages of existing therapies. Of particular need are agents which act by alternative mechanisms to modulate food intake and/or metabolism.

2. Neuropeptide Y ("NPY")

Throughout this application, various publications are referenced. The disclosure of these publications is hereby incorporated by reference into this application to describe more fully the art to which this invention pertains.

Neuropeptides are small peptides originating from large precursor proteins synthesized by peptidergic neurons and endocrine/paracrine cells. They hold promise for treatment of neurological, psychiatric, and endocrine disorders (De Wied, D. In: Neuropeptides: Basics and Perspectives (Elsevier, Amsterdam-New York-Oxford), 1990.). Often the precursors contain multiple biologically active peptides. There is great diversity of neuropeptides in the brain caused by alternative splicing of primary gene transcripts and differential precursor processing. The neuropeptide receptors serve to discriminate between ligands and to activate the appropriate signals. Thus, it is expected that the receptors for neuropeptides consist of a large number of members.

Neuropeptide Y (NPY), a 36-amino acid peptide, is the most abundant neuropeptide to be identified in mammalian brain. NPY is an important regulator in both the central and peripheral nervous systems (Heilig, M. and E. Widerlov. Neuropeptide Y: an overview of central distribution, functional aspects, and possible involvement of neuropsychiatric illnesses. Acta Psychiatr. Scand. 82:95-114 (1990).) and influences a diverse range of physiological parameters, including effects on psychomotor activity, food intake, central endocrine secretion, and vasoactivity in the cardiovascular system. High concentrations of NPY are found in the sympathetic nerves supplying the coronary, cerebral, and renal vasculature and has contributed to vasoconstriction. NPY binding sites have been identified in a variety of tissues, including spleen (Lundberg, J. M., A. Hemsen, O. Larsson, A. Rudehill, A. Saria, and B. Fredholm. Neuropeptide Y receptor in pig spleen: binding characteristics, reduction of cyclic AMP formation and calcium antagonist inhibition of vasoconstriction. Eur. J. Pharmacol. 145:21-29 (1988)), intestinal membranes, brain (Hinson, J., C. Rauh, and J. Coupet. Neuropeptide Y stimulates inositol phospholipid hydrolysis in rat brain microprisms. Brain RESPONSE. 446:379-382 (1988)), aortic smooth muscle (Mihara, S., Y. Shigeri, and M. Fujimoto. Neuropeptide Y-induced intracellular Ca2+ increase in vascular smooth muscle cells. FEBS Lett. 259: 79-82 (1989)), kidney, testis, and placenta (Dumont, Y., J. C. Martel, A. Fournier, S. St.-Pierre, and R. Quiron. Neuropeptide Y and neuropeptide Y receptor subtypes in brain and peripheral tissues. Prog. Neurobiol. 38:125-167 (1992)). In addition, binding sites have been reported in a number of rat and human cell lines (e.g. Y1 in SK-N-MC, MC-IXC, CHP-212, and PC12 cells; Y2 in SK-N—Be(2), CHP-234, and SMS-MSN) (Grundemar, L., S. P. Sheikh, and C. Wahlestedt, In: The Biology of Neuropeptide Y and Related Peptides. (Humana Press, Inc., Totawa, N.J.), (1992)).

NPY forms a family (called the pancreatic polypeptide family) together with pancreatic polypeptide (PP) and peptide YY (PYY) which all consist of 36 amino acids and have a common tertiary structure, the so-called PP-fold (Glover, I. D., D. J. Barlow, J. E. Pitts, S. P. Wood, I. J. Tickle, T. L. Blundell, K. Tatemoto, J. R. Kimmel, A. Wollmer, W. Strassburger, and Y.-S. Zhang. Conformational studies of the pancreatic polypeptide hormone family. Eur. J. Biochem. 142: 379-385 (1985)). Specific features of this family include a polyproline helix in residues 1 through 8, beta-turn in residues 9 through 14, an alpha-helix in residues 15 through 30, an outward-projecting C-terminus in residues 30 through 36, and a carboxy terminal amide which appears to be critical for biological activity (Schwartz, T. W., J. Fuhlendorff, L. L. Kjems, M. S. Kristensen, M. Vervelde, M. O'Hare, J. L. Krstenansky, and B. Bjoniholm. Signal epitopes in the three-dimensional structure of neuropeptide Y. Ann. N.Y. Acad. Sci. 611:35-47 (1990)). The C-terminal amidated residue of these peptides is essential for biological activity (Wahlestedt et al., 1986). Studies with peptide fragments of NPY have indicated that multiple NPY receptor subtypes exist (Wahlestedt, C., N. Yanaihara, and R. Hakanson. Evidence for different pre- and postjunctional receptors for neuropeptide Y and related peptides. Regul. Pept. 13:307-318 (1986)). Specifically, six receptor subtypes, denoted as Y1, Y2, Y3, Y4, Y5, and Y6, are understood to mediate the actions of NPY with each to-date, except for Y3, having been cloned.

The Y1, Y2, and Y5 receptors have been proposed to regulate feeding behavior, i.e. food intake, in subjects. A key pharmacological feature which distinguishes Y1 and Y2 is the fact that the Y1 receptor (and not the Y2 receptor) responds to an analog of NPY modified at residues 31 and 34 ([Leu31, Pro34]NPY), whereas the Y2 receptor (and not the Y1 receptor) has high affinity for the NPY peptide carboxyl-terminal fragment NPY-(13-36)(Fuhlendorff, J., U. Gether, L. Aakerlund, N. Langeland-Johansen, H. Thogersen, S. G. Melberg, U. B. Olsen, O. Thastrup, and T. W. Schwartz. [Leu31,Pro34] Neuropeptide Y: A specific Y1 receptor agonist. Proc. Natl. Acad. Sci. USA 87:182-186 (1990)).

One major drawback in designing NPY based drugs to target the Y1 and Y5 receptors, such as to regulate food intake, involves a difficulty in passing the drug through the blood brain barrier (BBB) on peripheral administration. The delivery of therapeutic proteins across the BBB is limited to size and biochemical properties of the respective proteins. Generally, diffusion of bioactive peptides is restricted to short ($\leq$6 amino acids) and highly lipophilic peptides.

Notably, it has been reported by the inventor that O-glycosylation of peptides, e.g. tripeptides, can promote BBB permeability, as well as increase proteolytic stability, enhance solubility, and may contribute to the stabilization of peptide structures (Gangadhar, B. P., S. D. S. Jois, and A. Balasubramaniam. Convenient high yield and stereoselective synthesis of O-glycopeptides using N-$\alpha$-Fmoc-Tyr/Ser[$\beta$-D-Glc (OAc)$_4$]OPfp generated in solution. Tetrahedron Letters 45:355-358 (2004)). As such, O-glycosylation of NPY analogs, specifically tripeptide analogs, such as those disclosed in U.S. Pat. Nos. 6,013,633 and 6,235,718 to Balasubramaniam et al., herein incorporated by reference, is expected to promote BBB entry of these novel tripeptides, and be useful in regulating appetite and in the treatment of weight problems (e.g. obesity, diabetes), eating disorders, and such.

In addition, it has been reported that the 11-amino acid human immunodeficiency virus (HIV) TAT protein transduction domain is able to cross the BBB, even when coupled with larger peptides (Kilic, U., E. Kilic, G. Dietz, and M. Bahr. Intravenous TAT-GDNF is protective after focal cerebral Ischemia in Mice. Stroke 34:1304-1310 (2003) and Schwarze S. R., A. Ho, B. A. Vocero-Akbani, and S. F. Dowdy. In vivo protein transduction: delivery of a biologically active protein into the mouse. Science 285: 1569-1572 (1999)). Notably, the inventor has extended certain tripeptides, such as those disclosed in U.S. Pat. Nos. 6,013,633 and 6,235,718 to Balasubramaniam et al., herein incorporated by reference, by conjugating them to the 11-amino acid TAT peptide, H-Tyr-Gly-Arg-Lys-Lys-Arg-Arg-Gln-Arg-Arg-Arg-(SEQ. ID. NO. 1), via a linker, to promote BBB entry of these novel peptides wherein they similarly are useful in regulating appetite and in the treatment of weight problems (e.g. obesity, diabetes), eating disorders, and such.

Experimental and clinical observations also have supported the concept that neuropeptides play central roles in neurotransmission as well as the regulation of secretory functions of adenohypophysial, pancreatic, adrenalcortical and gut cells. Among the thirty or so neuropeptides that have been implicated in neuronal function in the mammalian central nervous system, several have also been suggested to function as neurotransmitters or neuromodulators primarily in afferent neurons.

An additional action of NPY is to decrease cardiac contractility (inotropy). This is an extremely important action of NPY, because it is known that, under many circumstances in which inotropy is decreased, diseases of life-threatening importance, e.g. congestive heart failure and cardiogenic shock, are associated with probable increased release of NPY into the blood. Prevention of NPY release, using a presynaptic NPY agonist, or NPY's action, using a postsynaptic NPY antagonist, may be beneficial in these disease states.

NPY has also been reported to produce coronary artery vasoconstriction and thereby may decrease myocardial blood flow resulting in myocardial ischemia. Such a circumstance can result in angina pectoris or, under more severe circumstances, may result in myocardial infarction and death. In recent years, several classes of drugs have proven effective in dilating coronary arteries to prevent such events. The use of analogs of NPY are expected to prove useful in treatment of such problems.

U.S. Pat. No. 4,297,346 to Rips et al. discloses therapeutic agents referred to as 'pseudopeptides' being formed from at least one peptide radical connected by a peptide bond to a therapeutically active molecule or derivative of a therapeutically active molecule. The therapeutic agents of the invention may be in the form of derivatives such as salts, esters and amides. The basis of action of the agents of the invention is the ability of the agents of the invention to cross bodily biological barriers because of the basically peptide structure of the agents. The invention also includes the preparation of the agents of the invention.

U.S. Pat. No. 5,328,899 to Boublik et al., issued Jul. 12, 1994, discloses NPY peptide analogs. Human Neuropeptide Y (NPY) has the formula: H-Tyr-Pro-Ser-Lys-Pro-Asp-Asn-Pro-Gly-Glu-Asp-Ala-Pro-Ala-Glu-Asp-Met-Ala-Arg-Tyr-Tyr-Ser-Ala-Leu-Arg-His-Tyr-Ile-Asn-Leu-Ile-Thr-Arg-Gln-Arg-Tyr-NH2 (SEQ. ID. NO. 2). Porcine and rat NPY have the same sequence except for Leu instead of Met in the 17-position (SEQ. ID. NO. 3). Porcine PYY is homologous having 11 different residues. NPY analogs and N-terminally-shortened fragments, e.g. NPY(18-36), which contain one or more specific D-isomer substitutions for the naturally occurring residues (as well as pharmaceutically acceptable salts thereof), dispersed in a pharmaceutically acceptable liquid or solid carrier, can be administered to mammals, including humans, to substantially lower blood pressure over an extended period of time or to counteract hypertension.

U.S. Pat. No. 4,839,343 to Waeber et al., issued Jun. 13, 1989, discloses a preparation containing hexatriacontapeptides suitable for intravenous administration to human or other animal subjects which are effective in treating life-threatening hypotension as encountered in bacteremic, anaphylactic or cardiogenic shock.

Several references have disclosed CCK agonists or analogs of CCK-8. For example, U.S. Pat. No. 4,490,364 to Rivier, issued Dec. 25, 1984, discloses heptapeptide, octapeptide and nonapeptide analogs of CCK-8 as CCK agonists for stimulating gallbladder contractions, arresting the secretion of gastric acid and treating convulsions. J. D. Rosamond in European Patent Application EP381,340, published Aug. 8, 1990, and in European Patent Application EP268,297, published May 25, 1988, discloses hepta- and octapeptides with sulfate ester groups which are useful for treating obesity.

U.S. Pat. No. 5,270,302 to Shiosaki et al., issued Dec. 14, 1993, discloses derivatives of tetrapeptides as CCK agonists which are selective and potent Type-A CCK receptor agonists useful in the treatment of gastrointestinal disorders (including gallbladder disorders), central nervous system disorders, insulin-related disorders and pain, as well as in appetite regulation.

None of these references individually or collectively teach or suggest the present invention.

3. Peptide YY ("PYY")

Peptide YY (PYY) is a 36-residue peptide amide isolated originally from porcine intestine, and localized in the endocrine cells of the gastrointestinal tract and pancreas (Tatemoto et al. Proc. *Natl. Acad. Sci.* 79:2514, 1982). Peptide YY has N-terminal and C-terminal tyrosine amides; accordingly, these two tyrosines give PYY its name (Y represents the amino acid tyrosine in peptide nomenclature). In addition, PYY shares a number of central and peripheral regulatory roles with its homologous peptide Neuropeptide Y (NPY), which was originally isolated from porcine brain (Tatemoto, *Proc. Natl. Acad. Sci.* 79:5485, 1982). PYY is localized in intestinal cells; NPY, in contrast, is present in the submucous and myenteric neurons which innervate the mucosal and smooth muscle layers, respectively (Ekblad et al. *Neuroscience* 20:169, 1987). Both PYY and NPY are believed to inhibit gut motility and blood flow (Laburthe, *Trends Endocrinol. Metab.* 1:168, 1990), and they are also thought to attenuate basal (Cox et al. *Br. J. Pharmacol.* 101:247, 1990; Cox et al. *J. Physiol.* 398:65, 1988; Cox et al. Peptides 12:323, 1991; Friel et al. *Br. J. Pharmacol.* 88:425, 1986) and secretatogue-induced intestinal secretion in rats (Lundberg et al. *Proc. Natl. Acad. Sci. USA* 79:4471, 1982; Playford et al. *Lancet* 335: 1555, 1990) and humans (Playford et al., supra), as well as stimulate net absorption (MacFadyen et al. *Neuropeptides* 7:219, 1986). Elevated plasma PYY levels have been reported in individuals suffering from several conditions that cause diarrhea (Adrian et al. *Gastroenterology* 89:1070, 1985). Taken together, these observations suggest that PYY and NPY are released into the circulation after a meal (Adrian et al. *Gastroenterology* 89:1070, 1985: Balasubramaniam et al. *Neuropeptides* 14:209, 1989), and, thus may play a physiological role in regulating intestinal secretion and absorption, serving as natural inhibitors of diarrhea.

A high affinity PYY receptor system which exhibits a slightly higher affinity for PYY than NPY has been characterized in rat intestinal epithelia (Laburthe et al. *Endocrinology* 118:1910, 1986; Laburthe, *Trends Endocrinol. Metabl.* supra) and shown to be negatively coupled to adenylate cyclase (Servin et al. *Endocrinology* 124:692, 1989). Consistently, PYY exhibited greater antisecretory potency than NPY in voltage clamped preparations of rat small intestine (Cox et al. *J. Physiol.* supra), while C-terminal fragments of NPY were found to be less effective in their antisecretory potency than PYY (Cox et al. *Br. J. Pharmacol*, supra). Structure-activity studies using several partial sequences have led to the identification of PYY(22-36) as the active site for interacting with intestinal PYY receptors (Balasumbramaniam et al. *Pept. Res.* 1:32, 1988). This intestinal PYY-preferring receptor has now been cloned and shown to be identical to the $Y_2$ receptors cloned from the brain (Goumain et al. *Mol Pharmacol* 60:124-134, 2001).

In addition, PYY has been implicated in a number of physiological activities including nutrient uptake (see, e.g., Bilcheik et al. *Digestive Disease Week* 506:623, 1993), cell proliferation (see, e.g., Laburthe, *Trends Endocrinol. Metab.* 1:168, 1990; Voisin et al. *J. Bio. Chem,* 1993), lipolysis (see, e.g., Valet et al. *J. Clin. Invest.* 85:291, 1990), and vasoconstriction (see, e.g., Lundberg et al., *Proc. Natl. Acad. Sci, USA* 79:4471, 1982).

The amino acid sequences of porcine and human PYY are as follows:

porcine PYY: YPAKPEAPGEDASPEELSRYYASL-RHYLNLVTRQRY, (SEQ. ID. NO. 4)

human PYY: YPIKPEAPGEDASPEELNRYYASL-RHYLNLVTRQRY, (SEQ. ID. NO. 5). The amino acid sequences for dog PYY and for RAT PYY are the same as that of porcine YYY.

With respect to PYY, it has been reported previously that peripheral administration of PYY(3-36), a NPY $Y_2$-preferring ligand, can on peripheral administration attenuate food intake in normal and fasted mice and rats as well as in normal and obese humans (Nature 418:650-654; 2002, N Engl J Med 349:941-948; 2003). Accordingly, one advantage of using Y2 selective ligands is that they can suppress the food intake on peripheral administration, whereas Y1 and Y5 selective ligands, as described above, have to penetrate the BBB to modulate food intake.

In addition to interacting with the Y2 ligand, the PYY(3-36) can potently activate Y4 and Y5 receptors. Notably, the inventor has previously developed Y2 receptor selective agonists that are based on PYY(22-36) and PYY(25-36) (See U.S. Pat. Nos. 5,604,203, and 6,046,167 to Balasubramaniam) which are devoid of activities at the other NPY receptors including Y1, Y4, and Y5 at concentrations up to 20,000 nM. Most notably, the inventor recently tested the PYY(25-36) analogs N-α-Ac-[Trp$^{30}$]PYY(25-36)-NH$_2$ (SEQ. ID. NO. 6) and N-α-Ac-[Trp$^{27}$, ψ$^{35/36}$]PYY(25-36)-NH$_2$, (SEQ. ID. NO. 7), and the PYY(22-36) analog N-α-Ac[Nle$^{24,28}$, Trp$^{30}$, Nva$^{31}$, ψ$^{35/36}$]PYY(22-36)-NH$_2$ (SEQ. ID. NO. 8) [wherein ψ in the foregoing formulas is —CH$_2$—NH—] and unexpectedly found that these analogs could be used to control food intake in animals and humans. As such, it is expected that the PYY analogs and their deletion peptides, as disclosed in U.S. Pat. Nos. 5,604,203, and 6,046,167 to Balasubramaniam, which are herein incorporated by reference, could be used in an unexpected way to control food intake in animals and humans, and are expected to prove useful in the treatment of weight problems (e.g. obesity, diabetes), eating disorders, and such.

SUMMARY OF THE INVENTION

This invention relates generally to peptides including tripeptides and to methods for pharmaceutical treatment of mammals using such tripeptides and analogs thereof. More specifically, the invention is directed to neuropeptide Y ("NPY") receptor antagonists and agonists including O-glycosylated tripeptides, i.e. O-glycopeptides, and extended tripeptides, and their analogs, as well as to PYY analogs, to pharmaceutical compositions containing such tripeptides and PYY analogs, and to methods of treatment of mammals using such tripeptides and PYY analogs. In addition, the invention relates to methods of treatment of mammals using such tripeptides and PYY analogs for control of appetite, blood pressure, cardiovascular response, libido, and circadian rhythm.

In one aspect, the present invention features an O-glycosylated compound, i.e. O-glycopeptide, having the formula:

wherein:

each R1 and R2, independently, is H, C1-C12 alkyl (e.g., methyl), C6-C18 aryl (e.g., phenyl), C1-C18 acyl (e.g., formyl, acetyl, and myristoyl), C7-C18 aralkyl (e.g., benzyl), C7-C18 alkaryl (e.g., p-methylphenyl) or a dihydrotrigonellinate group;

A1 is a D or L-amino acid selected from Cys, Leu, Dap, Trp, Gln, a tethered amino acid with an indole ring (e.g., N-Me-Trp), Phe, Hyp, any Trp derivative (e.g., 2 chlorotroptophan, or Tcc); $C_\alpha$Me-Trp, $C_\alpha$Me-Gln, Des-amino-Trp, Pyr, Bth, Nal, Tcc, Asn, Nva, Abu, Ser, Tyr, N-Me-Tyr, $C_\alpha$Me-Tyr, Tic-OH, des-carboxylic-Tyr (tyramine), Phe, Trp, and Dip;

A2 is a D or L-amino acid selected from Gly, Cys, Trp, Arg, N-Me-Arg, $C_\alpha$Me-Arg, Orn, Cit, hArg(R)2 [where R is selected from hydrogen, alkyl, aryl, aralkyl, or alkylaryl], Lys-ε-NH—R [where R is selected from hydrogen, alkyl, aryl, aralkyl, or alkylaryl];

A3 is a D or L-amino acid selected from Ala, Glu, Tyr, N-Me-Tyr, $C_\alpha$Me-Tyr, Tic-OH, Tic, Dip, Trp, Phe, des-carboxylic-Tyr (tyramine), and Tyr-(R) [where R is hydrogen or a lipophilic group, e.g., myristoyl, cholesteryl, t.Bu, etc.];

One R6 is an acetylated or nonacetylated monosaccharide (e.g. glucose, fructose), or an acetylated or nonacetylated disaccharide (e.g. lactose, sucrose, maltose) with the other R6 being deleted;

W is —OH, —N—R3R4, or OR5 (where R3, R4, and R5, independently, is H, C1-C12 alkyl (e.g., methyl), C6-C18 aryl (e-g-, phenyl), C1-C12 acyl (e.g., formyl, acetyl, and myristoyl), C7-C18 aralkyl (e.g., benzyl), or C7-C18 alkaryl (e.g., p-methylphenyl); or a pharmaceutically acceptable salt thereof; and each bond between two amino acids or amino acid derivatives, represented by a dash ("-"), can be either a peptide bond or a pseudopeptide bond or a pharmaceutically acceptable salt thereof.

A preferred compound of formula (I) includes N-α-Ac-Trp-Arg-Tyr-[β-D-Glc]-NH₂, referred to as BG-7.

In another aspect, the invention features a compound having the formula:

Cyclo[A1(R6)-A2-A3(R6)], (II)

Cyclo[A1(R6)-A2-A3-A1(R6)-A2-A3(R6)], or (III)

Cyclo[A1(R6)-A2-A3(R6)-A3(R6)]-A2-A1(R6)]. (IV)

In another aspect, the invention features a compound having the formula:

Ac-[A1(R6)-A2-A3(R6)]$_n$-NH₂ (V)

(n=1, 2, or 3) (A Tandem Peptide)

With respect to compounds (II-V), R6 is an acetylated or nonacetylated monosaccharide (e.g. glucose, fructose), or an acetylated or nonacetylated disaccharide (e.g. lactose, sucrose, maltose) with no greater than two R6's, i.e. only one or two, being present in the compound. A1, A2, and A3 may be defined the same as A1, A2, and A3 of formula (I).

The novel extended tripeptides and their analogs, of the present invention, are produced by the coupling, via a linker or spacer, to, for example, the 11-amino acid TAT peptide H-Tyr-Gly-Arg-Lys-Lys-Arg-Arg-Gln-Arg-Arg-Arg-(SEQ. ID. NO. 1). In addition, the below identified extended tripeptides may include O-glycopeptides.

Accordingly, in another aspect, the invention features a compound having the formula:

R8-linker-[A1-A2-A3]$_n$-W (VI)

(n=1, 2, or 3)

R8 is H-Tyr-Gly-Arg-Lys-Lys-Arg-Arg-Gln-Arg-Arg-Arg-(i.e, the TAT peptide —SEQ. ID. NO. 1), H-[X(Y)]$_n$-[where X is Ser, Thr, or Tyr, Y is β-D-Glc or β-D-Gal, and n is 1, 2, or 3],

(SEQ. ID. NO. 9), Ac-Arg-Tyr-Arg-Gly-Asp-Leu-Gly-Leu-Gly-Arg-Arg (SEQ. ID. NO. 10), or

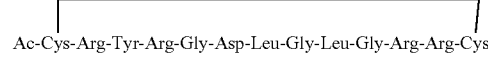

(SEQ. ID. NO. 11);

A1 is a D or L-amino acid selected from Cys, Leu, Dap, Trp, Gln, a tethered amino acid with an indole ring (e.g., N-Me-Trp), Phe, Hyp, any Trp derivative (e.g., 2 chlorotroptophan, or Tcc); $C_\alpha$Me-Trp, $C_\alpha$Me-Gln, Des-amino-Trp, Pyr, Bth, Nal, Tcc, Asn, Nva, Abu, Ser, Tyr, Tic-OH, Phe, Trp, and Dip;

Linker is a compound that forms a peptide bond with A1 and forms one of either a peptide or ester bond with R8;

A2 is a D or L-amino acid selected from Gly, Cys, Trp, Arg, N-Me-Arg, $C_\alpha$Me-Arg, Orn, Cit, hArg(R)2 [where R is selected from hydrogen, alkyl, aryl, aralkyl, or alkylaryl], Lys-ε-NH—R [where R is selected from hydrogen, alkyl, aryl, aralkyl, or alkylaryl];

A3 is a D or L-amino acid selected from Glu, Tyr, N-Me-Tyr, $C_\alpha$Me-Tyr, Tic-OH, Tic, Dip, Trp, Phe, des-carboxylic-Tyr (tyramine), and Tyr-(R) [where R is hydrogen or a lipophilic group, e.g., myristoyl, cholesteryl, t.Bu, etc.];

W is —OH, —N—R3R4, or OR5 (where R3, R4, and R5, independently, is H, C1-C12 alkyl (e.g., methyl), C6-C18 aryl (e-g-, phenyl), C1-C12 acyl (e.g., formyl, acetyl, and myristoyl), C7-C18 aralkyl (e.g., benzyl), or C7-C18 alkaryl (e.g., p-methylphenyl); or a pharmaceutically acceptable salt thereof; and each bond between two amino acids or amino acid derivatives, represented by a dash ("-"), can be either a peptide bond or a pseudopeptide bond or a pharmaceutically acceptable salt thereof.

Preferred compounds of formula (VI) include H-Tyr-Gly-Arg-Lys-Lys-Arg-Arg-Gln-Arg-Arg-Arg-NH—CH₂—CH₂—CO-Trp-Arg-Tyr-NH₂ (SEQ. ID. NO. 12), referred to as BG-116, H-Tyr-Gly-Arg-Lys-Lys-Arg-Arg-Gln-Arg-Arg-Arg-NH—CH₂—CH₂—CO-[Trp-Arg-Tyr]₂-NH₂ (SEQ. ID. NO. 13), referred to as BG-117, and H-Tyr-Gly-Arg-Lys-Lys-Arg-Arg-Gln-Arg-Arg-Arg-O—CH₂—CH₂—CO-Trp-Arg-Tyr-NH₂ (SEQ. ID. NO. 14), referred to as BG-120, as well as H-[Tyr(β-D-Glc)]-NH—CH₂—CH₂—CO-Trp-Arg-Tyr-HN₂ (SEQ. ID. NO. 15),

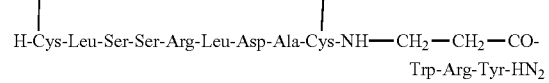

(SEQ. ID. NO. 16); Ac-Arg-Tyr-Arg-Gly-Asp-Leu-Gly-Leu-Gly-Arg-Arg-NH—CH$_2$—CH$_2$—CO-Trp-Arg-Tyr-HN$_2$ (SEQ. ID. NO. 17), and (SEQ. ID. NO. 18)

Ac-Cys-Arg-Tyr-Arg-Gly-Asp-Leu-Gly-Leu-Gly-Arg-Arg-Cys-NH—CH$_2$—CH$_2$—CO-Trp-Arg-Tyr-HN$_2$.

With respect to compound (VI), the linker advantageously is NH$_2$—CH$_2$—CH$_2$—COOH(β-Ala), HO—(CH$_2$)$_n$—COOH (n=1-5), or a D or L-amino acid including, but not limited to, Asp, Ala, Arg, Asn, Cys, Gly, Glu, Gln, His, Ile, Leu, Lys, Met, Phe, Pro, Ser, Thr, Trp, Tyr, and Val, and most advantageously β-Ala, wherein the linker forms a peptide bond with the di- or tripeptide moiety and forms one of either a peptide or ester bond with the TAT peptide moiety.

In another aspect, the invention features dimers of compounds having the formula (I-VI). Dimers may be prepared by dimerizing compounds of formula (I-X) with dicarboxylic acids (e.g., succinic acid), cystine, or diaminodicarboxylic acid (e.g., 2,6-diaminopimelic acid).

The PYY analogs of U.S. Pat. Nos. 5,604,203, and 6,046,167 to Balasubramaniam, hereby incorporated herein by reference, are further discussed below. Notably, the analogs of at least the following formulas (VII-VIII) optionally include at least one pseudopeptide bond between amino acids residues. By "psuedopeptide bond" is meant that the carbon atom participating in the bond between two residues is reduced from a carbonyl carbon to a methylene carbon, i.e., CH$_2$—NH; or less preferably that of CO—NH is replaced with any of CH$_2$—S, CH$_2$—CH$_2$, CH$_2$—O, or CH$_2$—CO. A psuedopeptide peptide bond is symbolized herein by "ψ". Preferably, the psuedopeptide bonds are located between one or more amino acid residues. In addition, such psuedopeptide bond analogs can be used to form dimeric analogs. A detailed discussion of psuedopeptide bonds is given in Coy et al. (1998) *Tetrahedron* 44:835-841.

Accordingly, in another aspect, the invention features a compound, having the formula:

(VII)

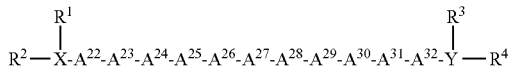

$$R^2-X-A^{22}-A^{23}-A^{24}-A^{25}-A^{26}-A^{27}-A^{28}-A^{29}-A^{30}-A^{31}-A^{32}-Y-R^4$$

wherein:

X is a chain of 0-5 amino acids, inclusive, where the N-terminal amino acid is bonded to R$^1$ and R$^2$ by the side chain of the N-terminal amino acid or by the nitrogen of the amino group of the N-terminal amino acid;

Y is a chain of 0-4 amino acids, inclusive, where the C-terminal amino acid has a carboxylamide group, which is independently bonded to R$^3$ and R$^4$, e.g.,

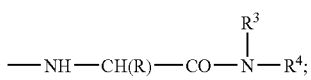

R$^1$ and R$^2$ are each independently bonded to the amino group of the N-terminal amino acid and selected from H, (C$_1$-C$_{12}$)alkyl (e.g. methyl), (C$_6$-C$_{18}$)aryl (e.g. phenyl, naphtaleneacetyl), (C$_1$-C$_{12}$)acyl (formyl, acetyl, and myristoyl), C$_7$-C$_{18}$ aralkyl (e.g. benzyl), and C$_7$-C$_{18}$ alkaryl (e.g. p-methlyphenyl);

R$^3$ and R$^4$ are each independently bonded to the amide group of the C-terminus amino acid, e.g.

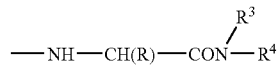

(where R denotes the side chain group of the amino acid, e.g. R=H in Gly, etc.), and selected from H, (C$_1$-C$_{12}$)alkyl (e.g. methyl), (C$_6$-C$_{18}$)aryl (e.g. phenyl, napthaleneacetyl), (C$_1$-C$_{12}$)acyl (formyl, acetyl, and myristoyl), C$_7$-C$_{18}$ aralkyl (e.g. benzyl), and C$_7$-C$_{18}$ alkaryl (e.g. p-methlyphenyl);

A$^{22}$ is an aromatic amino acid, Ala, Aib, Anb, N-Me-Ala or is deleted;

A$^{23}$ is Ser, Thr, Ala, Aib, N-Me-Ser, N-Me-Thr, N-Me-Ala or is deleted;

A$^{24}$ is Leu, Ile, Nle, Val, Trp, Gly, Nva, Aib, Anb, N-Me-Leu or is deleted;

A$^{25}$ is Arg, Lys, homo-Arg, diethyl-homo-Arg, Lys-ϵ-NH—R (where R is H, a branched or straight chain C$_1$-C$_{10}$ alkyl group, or an aryl group), Orn or is deleted;

A$^{26}$ is Ala, His, Thr, 3-Me-His, 1-Me-His, β-pyrazolylalaline, N-Me-His, Arg, Lys, homo-Arg, diethyl-homo-Arg, Lys-ϵ-NH—R (where R is H, a branched or straight chain C$_1$-C$_{10}$ alkyl group, an aryl group, or a pharmaceutically acceptable salt thereof), Orn or is deleted;

A$^{27}$ is an aromatic amino acid;

A$^{28}$ is Leu, Ile, Nle, Val, Trp, Aib, Anb or N-Me-Leu;

A$^{29}$ is Asn, Ala, Gln, Gly, Trp or N-Me-Asn;

A$^{30}$ is Leu, Ile, Nle, Nva, Fla, Val, Trp, Aib, Anb or N-Me-Leu;

A$^{31}$ is Val, Leu, Nle, Nva, Ile, Trp, Aib, Anb or N-Me-Val; and

A$^{32}$ is Thr, Ser, D-Trp, N-Me-Ser or N-Me-Thr.

In preferred embodiments, Y is A$^{33}$-A$^{34}$-A$^{35}$-A$^{36}$ wherein

A$^{33}$ is Arg, Lys, homo-Arg, diethyl-homo-Arg, Lys-ϵ-NH—R (where R is H, a branched or straight chain C$_1$-C$_{10}$ alkyl group, or an aryl group), Cys, or Orn A$^{34}$ is Cys, Gln, Asn, Ala, Gly, N-Me-Gln, Aib, or Anb;

A$^{35}$ is Arg, Lys, homo-Arg, diethyl-homo-Arg, Lys-ϵ-NH—R (where R is H, a branched or straight chain C$_1$-C$_{10}$ alkyl group, or an aryl group), Cys, or Orn; and A$^{36}$ is an aromatic amino acid, Cys, or a pharmaceutically acceptable salt thereof.

Most preferably, the compound of formula (VII) includes N-α-Ac[Nle$^{24,28}$, Trp$^{30}$, Nva$^{31}$, ψ$^{35/36}$]PYY(22-36)-NH$_2$ (SEQ. ID. NO. 8), referred to as BT-48, wherein ψ is —CH$_2$—NH—.

In another aspect, the invention features a compound having the formula:

(VIII)

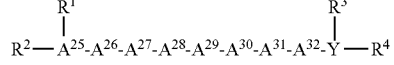

$$R^2-A^{25}-A^{26}-A^{27}-A^{28}-A^{29}-A^{30}-A^{31}-A^{32}-Y-R^4$$

wherein:
the N-terminal amino acid is bonded to $R^1$ and $R^2$; Y is a chain of 0-4 amino acids, inclusive, where the C-terminal amino acid is bonded to $R^3$ and $R^4$ by the side chain of the C-terminal amino acid or by the carbon of the carboxyl group of the C-terminal amino acid;

$R^1$ and $R^2$ are each independently bonded to the amino group of the N-terminal amino acid and selected from H, ($C_1$-$C_{12}$)alkyl (e.g. methyl), ($C_6$-$C_{18}$)aryl (e.g. phenyl, napthaleneacetyl), ($C_1$-$C_{12}$)acyl (formyl, acetyl, and myristoyl), $C_7$-$C_{18}$ aralkyl (e.g. benzyl), and $C_7$-$C_{18}$ alkaryl (e.g. p-methlyphenyl);

$R^3$ and $R^4$ are each independently bonded to the amide group of the C-terminus amino acid, e.g.

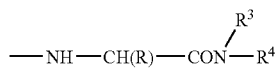

(where R denotes the side chain group of the amino acid, e.g. R=H in Gly, etc.), and selected from H, ($C_1$-$C_{12}$)alkyl (e.g. methyl), ($C_6$-$C_{18}$)aryl (e.g. phenyl, napthaleneacetyl), ($C_1$-$C_{12}$)acyl (formyl, acetyl, and myristoyl), $C_7$-$C_{18}$ aralkyl (e.g. benzyl), and $C_7$-$C_{18}$ alkaryl (e.g. p-methlyphenyl);

$A^{25}$ is Arg, Lys, homo-Arg, diethyl-homo-Arg, lys-ε-NH—R (where R is H, a branched or straight chain $C_1$-$C_{10}$ alkyl group, or an aryl group), Orn or is deleted;

$A^{26}$ is Ala, His, Thr, 3-Me-His, 1-Me-His, P-pyrozolylalanin, N-Me-His, Arg, Lys, homo-Arg, diethyl-homo-Arg, Lys-ε-NH—R (where R is H, a branched or straight chain $C_1$-$C_{10}$ alkyl group, or an aryl group), Orn or is deleted;

$A^{27}$ is an aromatic amino acid:

$A^{28}$ is Leu, Ile, Val, Trp Nle, Nva, Aib, Anb, or N-Me-Leu;

$A^{29}$ is Asn, Ala, Gln, Fly, Trp, or N-Me-Asn;

$A^{30}$ is Leu, Ile, Val, Trp, Nle, Nva, Aib, Anb, or N-Me-Leu;

$A^{31}$ is Val, Ile, Trp, Nva, Aib, Anb, or N-Me-Val; and $A^{32}$ is Thr, Ser, N-Me-Ser, N-Me-Thr, or D-Trp.

In preferred embodiments Y is $A^{33}$-$A^{34}$-$A^{35}$-$A^{36}$ wherein
$A^{33}$ is Arg, Lys, homo-Arg, diethyl-homo-Arg, Lys-ε-NH—R (where R is H, a branched or straight chain $C_1$-$C_{10}$ alkyl group, or $C_6$-$C_{18}$ aryl group), Cys, or Orn $A^{34}$ is Gln, Asn, Ala, Gly, N-Me-Gln, Aib, Cys, or Anb;

$A^{35}$ is Arg, Lys, homo-Arg, diethyl-homo-Arg, Lys-ε-NH—R (where R is H, a branched or straight chain $C_1$-$C_{10}$ alkyl group, or $C_6$-$C_{18}$ aryl group), Cys, or Orn; and $A^{36}$ is an aromatic amino acid, Cys, or a pharmaceutically acceptable salt thereof.

Most preferably, the compound of formula (VIII) includes N-α-Ac[$Trp^{27}$, $\psi^{35/36}$]PYY(25-36)-$NH_2$ (SEQ. ID. NO. 7), referred to as BT-56, and N-α-Ac[$Trp^{30}$]PYY(25-36)-$NH_2$ (SEQ. ID. NO. 6), referred to as BWX-115, wherein ψ in the foregoing formulas is —$CH_2$—NH—.

In other preferred embodiments, a compound of formula (I-VIII) may have one or more pseudopeptide bonds.

In another aspect, the invention features a compound having the formula of (I-VIII) conjugated to carriers.

In another aspect, the invention features a method of controlling the food intake, i.e. appetite, of a subject comprising administering to said subject the compound of formula (I-VIII).

In another aspect, the invention features a method of controlling the blood pressure of a subject experiencing hypertension.

In another aspect, the invention features a method of controlling a NPY physiological response in the cardiovascular system, including blood pressure, of a subject.

In other preferred embodiments, a therapeutically effective amount of a compound of formula (I-VIII) and a pharmaceutically acceptable carrier substance together form a therapeutic composition capable of suppressing an NPY mediated physiological response.

DETAILED DESCRIPTION OF THE INVENTION

Figure 1:
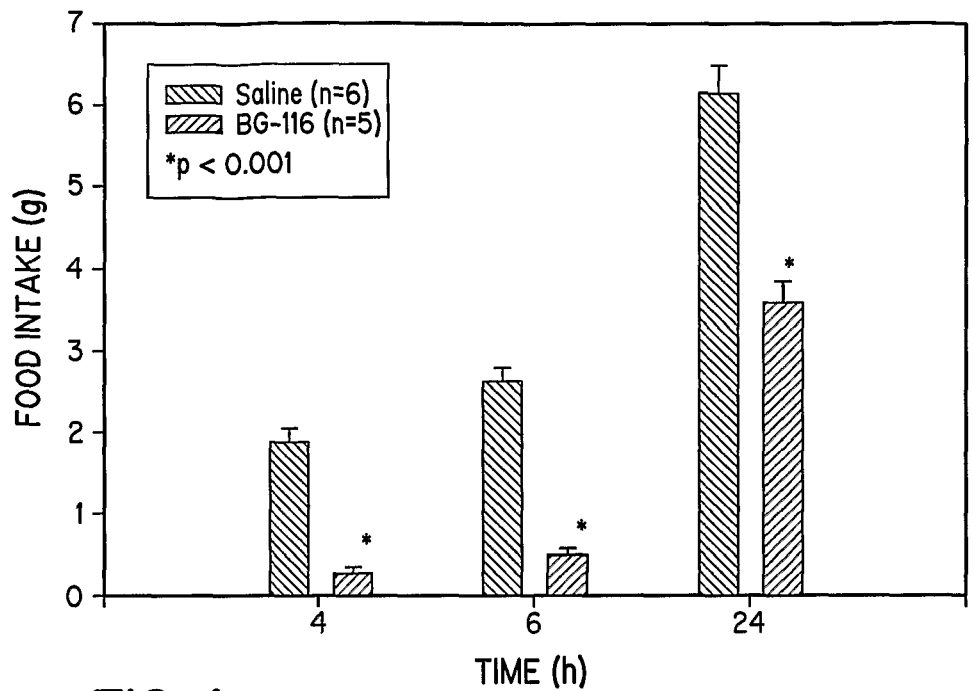
FIG. 1. A graph representing the feeding patterns of animals treated with an extended tripeptide by intraperitoneal injection. The compounds tested include control (saline) and BG-116 (H-Tyr-Gly-Arg-Lys-Lys-Arg-Arg-Gln-Arg-Arg-Arg-β-Ala-Trp-Arg-Tyr-$NH_2$) (SEQ. ID. NO. 12).

The present invention is directed to neuropeptide Y ("NPY") receptor antagonists and agonists including O-glycosylated tripeptides, i.e. O-glycopeptides, and extended tripeptides, and their analogs, as well as PYY analogs.

O-glycosylation of peptides, e.g. tripeptides, can promote BBB permeability, as well as increase proteolytic stability, enhance solubility, and may contribute to the stabilization of peptide structures (Gangadhar, B. P., S. D. S. Jois, and A. Balasubramaniam. Convenient high yield and stereoselective synthesis of O-glycopeptides using N-α-Fmoc-Tyr/Ser[β-D-Glc(OAc)$_4$]OPfp generated in solution. Tetrahedron Letters 45:355-358 (2004)). As such, O-glycosylation of NPY analogs, specifically tripeptide analogs, such as those disclosed in U.S. Pat. Nos. 6,013,633 and 6,235,718 to Balasubramaniam et al., herein incorporated by reference, is expected to promote BBB entry of these novel tripeptides, and be useful in regulating appetite and in the treatment of weight problems (e.g. obesity, diabetes), eating disorders, and such.

Accordingly, in one aspect, the present invention features an O-glycosylated compound having the formula:

wherein:
each R1 and R2, independently, is H, C1-C12 alkyl (e.g., methyl), C6-C18 aryl (e.g., phenyl), C1-C18 acyl (e.g., formyl, acetyl, and myristoyl), C7-C18 aralkyl (e.g., benzyl), C7-C18 alkaryl (e.g., p-methylphenyl) or a dihydrotrigonellinate group;
A1 is a D or L-amino acid selected from Cys, Leu, Dap, Trp, Gln, a tethered amino acid with an indole ring (e.g., N-Me-Trp), Phe, Hyp, any Trp derivative (e.g., 2 chlorotroptophan, or Tcc); $C_\alpha$Me-Trp, $C_\alpha$Me-Gln, Des-amino-Trp, Pyr, Bth, NaI, Tcc, Asn, Nva, Abu, Ser, Tyr, N-Me-Tyr, $C_\alpha$Me-Tyr, Tic-OH, des-carboxylic-Tyr (tyramine), Phe, Tip, and Dip;
A2 is a D or L-amino acid selected from Gly, Cys, Trp, Arg, N-Me-Arg, $C_\alpha$Me-Arg, Orn, Cit, hArg(R)2 [where R is selected from hydrogen, alkyl, aryl, aralkyl, or alkylaryl], Lys-ε-NH—R [where R is selected from hydrogen, alkyl, aryl, aralkyl, or alkylaryl];
A3 is a D or L-amino acid selected from Ala, Glu, Tyr, N-Me-Tyr, $C_\alpha$Me-Tyr, Tic-OH, Tic, Dip, Trp, Phe, des-carboxylic-Tyr (tyramine), and Tyr-(R) [where R is hydrogen or a lipophilic group, e.g., myristoyl, cholesteryl, t.Bu, etc.];
One R6 is an acetylyated or nonacetylyated monosaccharide (e.g. glucose, fructose), or an acetylated or nonacetylyated disaccharide (e.g. lactose, sucrose, maltose) with the other R6 being deleted;
W is —OH, —N—R3R4, or OR5 (where R3, R4, and R5, independently, is H, C1-C12 alkyl (e.g., methyl), C6-C18 aryl (e-g-, phenyl), C1-C12 acyl (e.g., formyl, acetyl, and myristoyl), C7-C18 aralkyl (e.g., benzyl), or $C_7$-C18 alkaryl (e.g., p-methylphenyl); or a pharmaceutically acceptable salt thereof; and
each bond between two amino acids or amino acid derivatives, represented by a dash ("-"), can be either a peptide bond or a pseudopeptide bond or a pharmaceutically acceptable salt thereof.

A preferred compound of formula (I) includes N-α-Ac-Trp-Arg-Tyr-[β-D-Glc]-NH$_2$, referred to as BG-7.

In another aspect, the invention features a compound having the formula:

Cyclo[A1(R6)-A2-A3(R6)],     (II)

Cyclo[A1(R6)-A2-A3-A1(R6)-A2-A3(R6)], or     (III)

Cyclo[A1(R6)-A2-A3(R6)-A3(R6)]-A2-A1(R6)].     (IV)

In another aspect, the invention features a compound having the formula:

Ac-[A1(R6)-A2-A3(R6)]$_n$-NH$_2$     (V)

(n=1, 2, or 3) (A Tandem Peptide)

With respect to compounds (II-V), R6 is an acetylyated or nonacetylyated monosaccharide (e.g. glucose, fructose), or an acetylated or nonacetylyated disaccharide (e.g. lactose, sucrose, maltose) with no greater than two R6's, i.e. only one or two, being present in the compound. A1, A2, and A3 may be defined the same as A1, A2, and A3 of formula (I).

In addition, it has been reported that the 11-amino acid human immunodeficiency virus (HIV) TAT protein transduction domain is able to cross the BBB, even when coupled with larger peptides (Kilic, U., E. Kilic, G. Dietz, and M. Bahr. Intravenous TAT-GDNF is protective after focal cerebral Ischemia in Mice. Stroke 34:1304-1310 (2003) and Schwarze S. R., A. Ho, B. A. Vocero-Akbani, and S. F. Dowdy. In vivo protein transduction: delivery of a biologically active protein into the mouse. Science 285: 1569-1572 (1999)). The inventor has extended certain tripeptides (and their analogs), such as those disclosed in U.S. Pat. Nos. 6,013,633 and 6,235,718 to Balasubramaniam et al., herein incorporated by reference, by conjugating them to the 11-amino acid TAT peptide, H-Tyr-Gly-Arg-Lys-Lys-Arg-Arg-Gln-Arg-Arg-Arg-(SEQ. ID. NO. 1), via a linker or spacer, to promote BBB entry of these novel peptides wherein they are useful in regulating appetite and in the treatment of weight problems (e.g. obesity, diabetes), eating disorders, and such. In addition, the below identified extended tripeptides may include O-glycopeptides.

Accordingly, in another aspect, the invention features a compound having the formula:

R8-linker-[A1-A2-A3]$_n$-W     (VI)

(n=1, 2, or 3)

R8 is H-Tyr-Gly-Arg-Lys-Lys-Arg-Arg-Gln-Arg-Arg-Arg-(i.e. the TAT peptide —SEQ. ID. NO. 1), H-[X(Y)]$_n$-[where X is Ser, Thr, or Tyr, Y is β-D-Glc or β-D-Gal, and n is 1, 2, or 3],

H-Cys-Leu-Ser-Ser-Arg-Leu-Asp-Ala-Cys (SEQ. ID. NO. 9),
Ac-Arg-Tyr-Arg-Gly-Asp-Leu-Gly-Leu-Gly-Arg-Arg(SEQ. ID. NO. 10), or
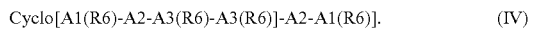
Ac-Cys-Arg-Tyr-Arg-Gly-Asp-Leu-Gly-Leu-Gly-Arg-Arg-Cys
(SEQ. ID. NO. 11);

A1 is a D or L-amino acid selected from Cys, Leu, Dap, Trp, Gln, a tethered amino acid with an indole ring (e.g., N-Me-Trp), Phe, Hyp, any Trp derivative (e.g., 2 chlorotroptophan, or Tcc); $C_\alpha$Me-Trp, $C_\alpha$Me-Gln, Des-amino-Trp, Pyr, Bth, NaI, Tcc, Asn, Nva, Abu, Ser, Tyr, Tic-OH, Phe, Tip, and Dip;
Linker is a compound that forms a peptide bond with A1 and forms one of either a peptide or ester bond with R8;
A2 is a D or L-amino acid selected from Gly, Cys, Trp, Arg, N-Me-Arg, $C_\alpha$Me-Arg, Orn, Cit, hArg(R)2 [where R is selected from hydrogen, alkyl, aryl, aralkyl, or alkylaryl], Lys-ε-NH—R [where R is selected from hydrogen, alkyl, aryl, aralkyl, or alkylaryl];
A3 is a D or L-amino acid selected from Glu, Tyr, N-Me-Tyr, $C_\alpha$Me-Tyr, Tic-OH, Tic, Dip, Trp, Phe, des-carboxylic-Tyr (tyramine), and Tyr-(R) [where R is hydrogen or a lipophilic group, e.g., myristoyl, cholesteryl, t.Bu, etc.];
W is —OH, —N—R3R4, or OR5 (where $R^3$, $R^4$, and $R^5$, independently, is H, C1-C12 alkyl (e.g., methyl), C6-C18 aryl (e-g-, phenyl), C1-C12 acyl (e.g., formyl, acetyl, and myristoyl), C7-C18 aralkyl (e.g., benzyl), or C7-C18 alkaryl (e.g., p-methylphenyl); or a pharmaceutically acceptable salt thereof; and
each bond between two amino acids or amino acid derivatives, represented by a dash ("-"), can be either a peptide bond or a pseudopeptide bond or a pharmaceutically acceptable salt thereof.

Preferred compounds of formula (VI) include H-Tyr-Gly-Arg-Lys-Lys-Arg-Arg-Gln-Arg-Arg-Arg-NH—CH$_2$—CH$_2$—CO-Trp-Arg-Tyr-NH$_2$ (SEQ. ID. NO. 12), referred to as BG-116, H-Tyr-Gly-Arg-Lys-Lys-Arg-Arg-Gln-Arg-Arg-Arg-NH—CH$_2$—CH$_2$—CO-[Trp-Arg-Tyr]$_2$-NH$_2$ (SEQ. ID. NO 13), referred to as BG-117, and H-Tyr-Gly-Arg-Lys-Lys-Arg-Arg-Gln-Arg-Arg-Arg-O—CH$_2$—CO-Trp-Arg-Tyr-NH$_2$ (SEQ. ID. NO. 14), referred to as BG-120, as well as H-[Tyr(β-D-Glc)]-NH—CH$_2$—CH$_2$—CO-Trp-Arg-Tyr-HN$_2$ (SEQ. ID. NO. 15),

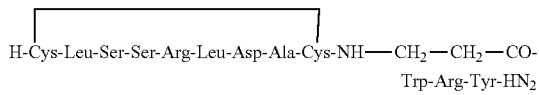

(SEQ. ID. NO. 16); Ac-Arg-Tyr-Arg-Gly-Asp-Leu-Gly-Leu-Gly-Arg-Arg-NH—CH$_2$—CH$_2$—CO-Trp-Arg-Tyr-HN$_2$ (SEQ. ID. NO. 17), and

(SEQ. ID. NO. 18)

With respect to compound (VI), the linker advantageously is NH$_2$—CH$_2$—CH$_2$—COOH(β-Ala), HO—(CH$_2$)$_n$—COOH (n=1-5) (e.g., HO—CH$_2$—COOH (glycolic acid)), or a D or L-amino acid including, but not limited to, Asp, Ala, Arg, Asn, Cys, Gly, Glu, Gln, His, Ile, Leu, Lys, Met, Phe, Pro, Ser, Thr, Trp, Tyr, and Val, and most advantageously β-Ala, wherein the linker forms a peptide bond with the di- or tripeptide moiety and forms one of either a peptide or ester bond with the TAT peptide moiety.

The PYY analogs of U.S. Pat. Nos. 5,604,203, and 6,046,167 to Balasubramaniam, are hereby incorporated herein by reference, and further discussed below. Notably, the analogs of at least the following formulas (i-VI) optionally include at least one pseudopeptide bond between amino acids residues. By "psuedopeptide bond" is meant that the carbon atom participating in the bond between two residues is reduced from a carbonyl carbon to a methylene carbon, i.e., CH2-NH; or less preferably that of CO—NH is replaced with any of CH$_2$—S, CH$_2$—CH$_2$, CH$_2$—O, or CH$_2$—CO. A psuedopeptide peptide bond is symbolized herein by "ψ". Preferably, the psuedopeptide bonds are located between one or more amino acid residues. In addition, such psuedopeptide bond analogs can be used to form dimeric analogs. A detailed discussion of psuedopeptide bonds is given in Coy et al. (1998) *Tetrahedron* 44:835-841.

Accordingly, in another aspect, the invention features a compound having the formula:

(VII)

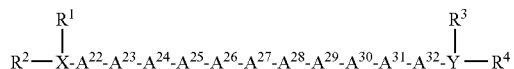

wherein

X is a chain of 0-5 amino acids, inclusive, where the N-terminal amino acid is bonded to R$^1$ and R$^2$ by the side chain of the N-terminal amino acid or by the nitrogen of the amino group of the N-terminal amino acid;

Y is a chain of 0-4 amino acids, inclusive, where the C-terminal amino acid has a carboxyl amide group, which is independently bonded to R$^3$ and R$^4$, e.g.,

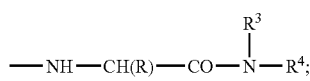

R$^1$ and R$^2$ are each independently bonded to the amino group of the N-terminal amino and selected from H, (C$_1$-C$_{12}$) alkyl (e.g. methyl), (C$_6$-C$_{18}$)aryl (e.g. phenyl, napthaleneacetyl), (C$_1$-C$_{12}$)acyl (formyl, acetyl, and myristoyl), C$_7$-C$_{18}$ aralkyl (e.g. benzyl), and C$_7$-C$_{18}$ alkaryl (e.g. p-methlyphenyl);

R$^3$ and R$^4$ are each independently bonded to the amide group of the C-terminus amino acid, e.g.

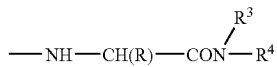

(where R denotes the side chain group of the amino acid, e.g. R═H in Gly, etc.), and selected from H, (C$_1$-C$_{12}$)alkyl (e.g. methyl), (C$_6$-C$_{18}$)aryl (e.g. phenyl, napthaleneacetyl), (C$_1$-C$_{12}$)acyl (formyl, acetyl, and myristoyl), C$_7$-C$_{18}$ aralkyl (e.g. benzyl), and C$_7$-C$_{18}$ alkaryl (e.g. p-methlyphenyl);

A$^{22}$ is an aromatic amino acid, Ala, Aib, Anb, N-Me-Ala or is deleted;

A$^{23}$ is Ser, Thr, Ala, Aib, N-Me-Ser, N-Me-Thr, N-Me-Ala or is deleted;

A$^{24}$ is Leu, Ile, Nle, Val, Trp, Gly, Nva, Aib, Anb, N-Me-Leu or is deleted;

A$^{25}$ is Arg, Lys, homo-Arg, diethyl-homo-Arg, Lys-pε-NH—R (where R is H, a branched or straight chain C$_1$-C$_{10}$ alkyl group, or an aryl group), Orn or is deleted;

A$^{26}$ is Ala, His, Thr, 3-Me-His, 1-Me-His, β-pyrazolylalaline, N-Me-His, Arg, Lys, homo-Arg, diethyl-homo-Arg, Lys-ε-NH—R (where R is H, a branched or straight chain C$_1$-C$_{10}$ alkyl group, an aryl group, or a pharmaceutically acceptable salt thereof), Orn or is deleted;

A$^{27}$ is an aromatic amino acid;

A$^{28}$ is Leu, Ile, Nle, Val, Trp, Aib, Anb or N-Me-Leu;

A$^{29}$ is Asn, Ala, Gln, Gly, Trp or N-Me-Asn;

A$^{30}$ is Leu, Ile, Nle, Nva, Fla, Val, Trp, Aib, Anb or N-Me-Leu;

A$^{31}$ is Val, Leu, Nle, Nva, Ile, Trp, Aib, Anb or N-Me-Val; and

A$^{32}$ is Thr, Ser, D-Trp, N-Me-Ser or N-Me-Thr.

In preferred embodiments, Y is A$^{33}$-A$^{34}$-A$^{35}$-A$^{36}$ wherein

A$^{33}$ is Arg, Lys, homo-Arg, diethyl-homo-Arg, Lys-ε-NH—R (where R is H, a branched or straight chain C$_1$-C$_{10}$ alkyl group, or an aryl group), Cys, or Orn A$^{34}$ is Cys, Gln, Asn, Ala, Gly, N-Me-Gln, Aib, or Anb;

A$^{35}$ is Arg, Lys, homo-Arg, diethyl-homo-Arg, Lys-ε-NH—R (where R is H, a branched or straight chain C$_1$-C$_{10}$ alkyl group, or an aryl group), Cys, or Orn; and A$^{36}$ is an aromatic amino acid, Cys, or a pharmaceutically acceptable salt thereof.

Most preferably, the compound of formula (VII) includes N-α-Ac[Nle$^{24,28}$, Trp$^{30}$, Nva$^{31}$, ψ$^{135/36}$]PYY(22-36)-NH$_2$ (SEQ. ID. NO. 8), referred to as BT-48, wherein ψ is —CH2-NH—.

In another aspect, the invention features a compound having the formula:

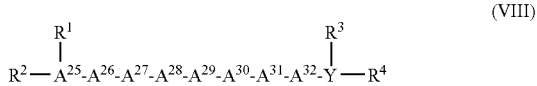

(VIII)

wherein:
the N-terminal amino acid is bonded to $R^1$ and $R^2$; Y is a chain of 0-4 amino acids, inclusive, where the C-terminal amino acid is bonded to $R^3$ and $R^4$ by the side chain of the C-terminal amino acid or by the carbon of the carboxyl group of the C-terminal amino acid;

$R^1$ and $R^2$ are each independently bonded to the amino group of the N-terminal amino and selected from H, ($C_1$-$C_{12}$) alkyl (e.g. methyl), ($C_6$-$C_{18}$)aryl (e.g. phenyl, napthaleneacetyl), ($C_1$-$C_{12}$)acyl (formyl, acetyl, and myristoyl), $C_7$-$C_{18}$ aralkyl (e.g. benzyl), and $C_7$-$C_{18}$ alkaryl (e.g. p-methylphenyl);

$R^3$ and $R^4$ are each independently bonded to the amide group of the C-terminus amino acid, e.g.

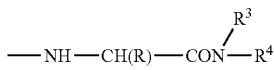

(where R denotes the side chain group of the amino acid, e.g. R=H in Gly, etc.), and selected from H, ($C_1$-$C_{12}$)alkyl (e.g. methyl), ($C_6$-$C_{18}$)aryl (e.g. phenyl, napthaleneacetyl), ($C_1$-$C_{12}$)acyl (formyl, acetyl, and myristoyl), $C_7$-$C_{18}$ aralkyl (e.g. benzyl), and $C_7$-$C_{18}$ alkaryl (e.g. p-methylphenyl);

$A^{25}$ is Arg, Lys, homo-Arg, diethyl-homo-Arg, lys-ϵ-NH—R (where R is H, a branched or straight chain $C_1$-$C_{10}$ alkyl group, or an aryl group), Orn or is deleted;

$A^{26}$ is Ala, His, Thr, 3-Me-His, 1-Me-His, β-pyrozolylalanin, N-Me-His, Arg, Lys, homo-Arg, diethyl-homo-Arg, Lys-ϵ-NH—R (where R is H, a branched or straight chain $C_1$-$C_{10}$ alkyl group, or an aryl group), Orn or is deleted;

$A^{27}$ is an aromatic amino acid:

$A^{28}$ is Leu, Ile, Val, Trp Nle, Nva, Aib, Anb, or N-Me-Leu;

$A^{29}$ is Asn, Ala, Gin, Fly, Trp, or N-Me-Asn;

$A^{30}$ is Leu, Ile, Val, Trp, Nle, Nva, Aib, Anb, or N-Me-Leu;

$A^{31}$ is Val, Ile, Trp, Nva, Aib, Anb, or N-Me-Val;

$A^{32}$ is Thr, Ser, N-Me-Ser, N-Me-Thr, or D-Trp;

In preferred embodiments Y is $A^{33"}$-34-$A^{35}$-$A^{36}$ wherein
$A^{33}$ is Arg, Lys, homo-Arg, diethyl-homo-Arg, Lys-ϵ-NH—R (where R is H, a branched or straight chain $C_1$-$C_{10}$ alkyl group, or $C_6$-$C_{18}$ aryl group), Cys, or Orn
$A^{34}$ is Gln, Asn, Ala, Gly, N-Me-Gin, Aib, Cys, or Anb;
$A^{35}$ is Arg, Lys, homo-Arg, diethyl-homo-Arg, Lys-ϵ-NH—R (where R is H, a branched or straight chain $C_1$-$C_{10}$ alkyl group, or $C_6$-$C_{18}$ aryl group), Cys, or Orn; and
$A^{36}$ is an aromatic amino acid, Cys, or a pharmaceutically acceptable salt thereof.

Most preferably, the compound of formula (VI) includes N-α-Ac[Trp$^{27}$, ψ$^{35/36}$]PYY(25-36)-NH$_2$ (SEQ. ID. NO. 7), referred to as BT-56, and N-α-Ac[Trp$^{30}$]PYY(25-36)-NH$_2$ (SEQ. ID. NO. 6), referred to as BWX-115, wherein ψ in the foregoing formulas is —CH2-NH—.

In another aspect, the invention features dimers of compounds having the formula (I-VIII) prepared by dimerizing the compound with at least dicarboxylic acids (e.g., succinic acid), cystine, or diaminodicarboxylic acid (e.g., 2,6-diaminopimelic acid).

In other preferred embodiments, a compound of formula (I-VIII) may have one or more pseudopeptide bonds.

In another aspect, the invention features a compound having the formula of (I-VIII) could be conjugated to carriers, e.g., cationized albumin (Endocrinology 126:977-984 (1990); J. Pharmacol Exp. Therao. 268:791-796 (1994), incorporated herein by reference in their entirety) or polylysine, e.g., MAP.

In another aspect, the invention features a method of controlling the food intake, i.e. appetite, of a subject comprising administering to said subject the compound of formula (I-VIII).

In other preferred embodiments, a therapeutically effective amount of a compound of formula (I-VIII) and a pharmaceutically acceptable carrier substance, e.g., magnesium carbonate or lactose, together form a therapeutic composition capable of suppressing an NPY mediated physiological response. This composition can be in the form a pill, tablet, capsule, liquid, or sustained released tablet for oral administration; or a liquid for nasal administration as drops or spray; or a liquid for intravenous, subcutaneous, parenteral, or intraperitoneal administration.

Another preferred form for administration includes a biodegradable sustained-release composition for intramuscular administration to a subject in need of the composition. Preferably, the composition includes a lipophilic salt and is suitable for administration in the form of an oil emulsion or dispersion to a subject in need of the composition.

In yet another aspect, the invention features methods for controlling an NPY mediated physiological response in a subject; such methods involve administering one or more of the above mentioned compounds to a subject in a dosage effective to control blood pressure, the appetite, the libido, cardiovascular function, and circadian rhythm.

The symbol A1, A2, A3, and the like; and Tyr, Lys or the like, as found in a peptide sequence herein stands for an amino acid residue, e.g., =N—CH(R)—CO— when it is at the N-terminus, or —NH—CH(R)—CO— when it is at any other position, where R denotes the side chain (or identifying group) of an amino acid or its residue. For example, R is $CH_2COOH$ for Asp, R is —H for Gly, R is —$CH_2OH$ for Ser, R is —CH3 for Ala and R is —$CH_2CH_2CH_2CH_2NH_2$ for Lys.

As set forth above and for convenience in describing this invention, the conventional and nonconventional abbreviations for the various amino acids are used. They are familiar to those skilled in the art; but for clarity are listed below. All peptide sequences mentioned herein are written according to the usual convention whereby the N terminal amino acid is on the left and the C-terminal amino acid is on the right. A short line between two amino acid residues indicates a peptide bond.

Abbreviations (Common):
Asp=D=Aspartic Acid
Ala=A=Alanine
Arg=R=Arginine
Asn=N=Asparagine
Cys=C=Cysteine
Gly=G=Glycine
Glu=E=Glutamic Acid
Gln=Q=Glutamine
His=H=Histidine
Ile=1=Isoleucine
Leu=L=Leucine
Lys=K=Lysine
Met=M=Methionine
Phe=F=Phenylalanine
Pro=P=Proline
Ser=S=Serine
Thr=T=Threonine Trp=W=Tryptophan
Tyr=Y=Tyrosine
Val=V=Valine Abbreviations (Uncommon):
Aoc=8-aminooctanoic acid
Orn=Ornithine
Nal=2-napthylalanine
Thi=2-thienylalanine
Pcp=4-chlorophenylalanine
Bth=3-benzothienylalanine
Bip=4,4'-biphenylalanine
Tic=tetrahydroisoquinoline-3-carboxylic acid
Aib=aminoisobutyric acid
Anb=alpha-aminonormalbutyric acid
$Ac_6c$=1-aminocyclohexanecarboxylic acid
D-Pal=beta-(3-pyridyl)alanine;
Tcc=tetrahydrocarbolenecarboxylic acid
Abu=α-aminonormalbutyric acid
$hArg(Pr)_2$=N,N'-guanidino-(dipropyl)-homoarginine
Tic-OH=1,2,3,4 tetrahydroisoquinoline-7-hydroxy-3-carboxylic acid
Dip=3,3-diphenylalanine
2-Nal=3(2-naphthylalanine)
Tfp=Paratrifluoromethyl phenylalanine
Fla=3-(9-Fluorenyl)alanine
Flg=9-Fluorenylglycine
Cit=Citruline
Adp=2,5-diaminoadipic acid
Pim=2,6-diaminopimelicacid
Sub=2,7-diaminosuberic acid
Nle=Norleucine
Nva=Norvaline
Thz=4-Thiazolylalanine
Dpr-Dap=2,3-diaminopropionic acid
Pyr=Pyroglutamic acid
Tip=1,2,3,4-tetrahydronorhannan-3-carboxylic acid Other Abbreviations:
Glc=Glucose
Lac=Lactose
Gal=Galactose
Fmoc=N-(9-fluorenyl)methoxycarbonyl The compounds of the invention are useful in treating any number of illnesses that involve eating disorders, cardiovascular function, alterations in sexual function, as well as disorders of sleep and circadian rhythms (see, e.g., *Harrison's Principles of Internal Medicine*, McGraw-Hill Inc., New York, 12th ed.).

Other features and advantages of the invention will be apparent from the following description of the preferred embodiments thereof, and from the claims.

The present invention is also directed to pharmaceutical compositions comprising a therapeutically-effective amount of a compound of formula (I-VIII) and a pharmaceutically-acceptable carrier or diluent, as well as to a method of regulating appetite in humans and lower mammals, by administration of a compound of formula (I-VIII).

The terms "C2-C4-alkenyl" and "C2-C6-alkenyl" as used herein refer to a 2 to 4 to 6 straight- or branched-chain of carbon atoms which contains a carbon-carbon double bond, such as allyl, propenyl, butanol, isoprenyl and the like.

The terms "C1-C18-alkyl" as used herein refer to straight or branched chain alkyl radicals having from 1 to 18 carbon atoms including, but not limited to, methyl, ethyl, propyl, isopropyl, butyl, isobutyl, sec-butyl, pentyl, neopentyl hexyl, and the like.

The term "C6-C18-aryl" as used herein refers to phenyl or to a "bicyclic carbocyclic" group or "bicyclic carbocycle" having two fused carbocyclic rings, each ring having 5, 6 or 7 carbon atoms, and each ring being fully saturated, partially saturated or aromatic. Bicyclic carbocyclic groups include, but are not limited to, naphthyl, tetrahydronaphthyl, decalin, indanyl, indenyl and the like.

The term "C7-C18-arylalkyl" as used herein refers to an aryl group appended to a C1-C4-alkyl radical including, but not limited to, benzyl, phenethyl, naphthylmethyl and the like.

The term "bicyclic heterocycle" as used herein refers to a group having two fused rings, one or both of which are heterocyclic rings as defined herein. When both rings are not heterocyclic, the other ring is carbocyclic and is saturated, partially saturated or aromatic, preferably a benzene ring. Bicyclic heterocyclic groups can be unsubstituted or mono-substituted or disubstituted with substituents independently selected from hydroxy, halo, oxo (=O), amino, C1-C4-alkylamino, di-(C1-C4)-alkylamino, C1-C4-alkoxy, thio-C1-C4-alkoxy, carboxy, C1-C4-alkoxycarbonyl, C1-C4-alkyl, C3-C8-cycloalkyl, —$OSO_3H$ and halo-C1-C4-alkyl. Examples of bicyclic heterocycles include indole, 5-hydroxyindole, quinoline, isoquinoline, tetrahydroisoquinoline, quinoxaline, benzimidazole, benzofuran, and the like.

The term "cyclo-C3-C10-alkyl" as used herein refers to an aliphatic monocyclic of 3 to 10 or bicyclic group having 6 to 10 carbon atoms including, but not limited to, cyclopropyl, cyclobutyl, cyclopentyl, cyclohexyl, cyclooctyl, adamantyl, and the like.

The term "halo" or "halogen" as used herein refers to chloro, bromo, iodo or fluoro.

The term "halo-C1-C4-alkyl" as used herein refers to a lower alkyl radical in which one to three hydrogen atoms have been replaced by a halogen including, but not limited to, chloromethyl, 2-fluoroethyl, trifluoromethyl and the like.

The term "monocyclic heterocyclic group" or "monocyclic heterocycle" as used herein refers to any 3- or 4-membered ring containing a heteroatom selected from oxygen, nitrogen and sulfur, or a 5- or 6-membered ring containing carbon atoms and one, two or three nitrogen atoms; one nitrogen and one sulfur atom; or one nitrogen and one oxygen atom; wherein the 5-membered ring has 0-2 double bonds and the 6-membered ring has 0-3 double bonds; wherein the nitrogen and sulfur heteroatoms may optionally be oxidized; and wherein the nitrogen heteroatom may optionally be quaternized. Heterocycles include, but are not limited to, pyridyl, imidazolyl, furyl, thienyl, pyrazinyl, pyrrolyl, pyrimidyl and the like. Heterocyclics may be unsubstituted or mono- or disubstituted with substituents independently selected from hydroxy, halo, oxo (=O), amino, C1-C4-alkylamino, (C1-C4)2-alkylamino, C1-C4-alkoxy, thio-C1-C4-alkoxy, carboxy, C1-C4-alkoxycarbonyl, C1-C4-alkyl, C3-C8-cycloalkyl, —$OSO_3H$ and halo-C1-C4-alkyl.

The term "O-glycopeptide" as used herein refers to a compound consisting of a carbohydrate, i.e. a saccharide, such as a mono- or disaccharide, linked to a peptide, advantageously a di- or tripeptide, composed of L- and/or D-amino acids including derivatives thereof, via a glycosyl linkage (O—) to an amino acid.

The term "monosaccharide" as used herein refers to any straight or branched-chain, or cyclic, i.e. ring-structured, simple sugar having the general formula $(CH_2O)_x$ where n can be 3-7, and further refers to any configurational isomers including enantiomers, diastereomers, and anomers, which account for the α or β, and D or L designations, as well as derivatives thereof. Of preference are the 6-carbon ring structures, such as glucose, more preferably β-D-glucose.

The term "dissaccharide" as used herein refers to a compound made up of two, ring-structured monosaccharide residues connected via a glycosidic bond. Of preference is lactose.

The term "peptide bond" as used herein refers to the chemical bond between carbon and nitrogen in the bivalent group CONH that unites amino acid residues in a peptide.

The term "ester bond" as used herein refers to the chemical bond between the carbon at the C-terminus of the TAT peptide and the oxygen of the linker compound wherein the coupled compounds can be represented generally by the formula RCOOR' with RCO representing the TAT peptide moeity and OR' representing the linker.

In addition, the above compounds may contain two or more asymmetric carbon atoms and thus can exist as pure diastereomers, mixtures of diastereomers, diastereomeric racemates or mixtures of diastereomeric racemates. As such, the present invention includes within its scope all of the isomeric forms. In keeping with standard peptide nomenclature, J. Biol. Chem., 1969, 243:3557-59, abbreviations for amino acid residues are used herein.

It is noted that all amino acid residue sequences are represented herein by formulae whose left to right orientation is in the conventional direction of amino-terminus to carboxy-terminus.

Administration

The amount of active ingredient that may be combined with the carrier materials to produce a single dosage form will vary depending upon the host treated, the particular treatment and the particular mode of administration.

It will be understood, however, that the specific dose level for any particular patient will depend upon a variety of factors including the activity of the specific compound employed, the age, body weight, general health, sex, diet, time of administration, rate of excretion, drug combination, and the severity of the particular disease undergoing therapy.

However, generally speaking the following guidelines will suffice. When a compound of formula (I) is used as an agonist of NPY in a human subject, the total daily dose administered in single or divided doses may be in amounts, for example, from 0.001 to 1000 mg a day and more usually 1 to 1000 mg. Dosage unit compositions may contain such amounts of sub-multiples thereof to make up the daily dose.

The compounds useful in the present inventive method may be administered by any suitable means. One skilled in the art will appreciate that many suitable methods of administering the compounds to an animal in the context of the present invention, in particular a human, are available, and, although more than one route may be used to administer a particular compounds, a particular route of administration may provide a more immediate and more effective reaction than another route.

The composition according to the present invention may be formulated for administration by any suitable route such as the oral, rectal, nasal, topical (dermal) or parenteral administration route. Thus, the composition may be in the form of tablets, capsules, suspensions, emulsions, solutions, injectables, suppositories, sprays, aerosols and in other suitable form.

Formulations for oral use include tablets which contain the active ingredient in admixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, potato starch or alginic acid; binding agents, for example, starch, gelatin or acacia; and lubricating agents, for example, magnesium stearate, stearic acid or talc. Other pharmaceutically acceptable excipients can be colorants, flavoring agents, plasticizers, humectants etc. The tablets may be uncoated or they may be coated by known techniques, optionally to delay disintegration and absorption in the gastrointestinal tract and thereby provide a sustained action over a longer period. For example, a time delay material such as glyceryl monostearate or glyceryl distearate may be employed.

Formulations for oral use may also be presented as chewing tablets, or as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Powders, dispersible powders or granules suitable for preparation of an aqueous suspension by addition of water are also convenient dosage forms of the present invention. Formulation as a suspension provide the active ingredient in admixture with a dispersing or wetting agent, suspending agent and one or more preservatives. Suitable dispersing or wetting agents are, for example, naturally-occurring phosphatides, as e.g. lecithin, or condensation products of ethylene oxide with e.g. a fatty acid, a long chain aliphatic alcohol or a partial ester derived from fatty acids and a hexitol or a hexitol anhydrides, for example, polyoxyethylene stearate, polyoxyethylene sorbitol monooleate, polyoxyethylene sorbitan monooleate etc. Suitable suspending agents are, for example, sodium carboxymethylcellulose, methylcellulose, sodium alginate etc.

The present agents can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the tetrapeptide of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., Methods in Cell Biology, Volume XIV, Academic Press, New York, N.Y. (1976), p. 33 et seq.

The pharmaceutical formulation may also be administered parenterally (intravenous, intramuscular, subcutaneous or the like) in dosage forms or formulations containing conventional, non-toxic pharmaceutically acceptable carriers and adjuvants. The formulation and preparation of such compositions is well-known to those skilled in the art of pharmaceutical formulation.

For parenteral use, the pharmaceutical compositions according to the invention may comprise the thermogenic compounds in the form of a sterile injection. To prepare such a composition, the compounds are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate.

For the rectal application, suitable dosage forms for a composition according to the present invention include suppositories (emulsion or suspension type), and rectal gelatin capsules (solutions or suspensions). In a typical suppository formulation, the compounds are combined with an appropriate pharmaceutically acceptable suppository base such as cocoa butter, esterified fatty acids, glycerinated gelatin, and various water-soluble or dispersible bases like polyethylene glycols and polyoxyethylene sorbitan fatty acid esters. Various additives like e.g. enhancers or surfactants may be incorporated.

For the nasal application typical dosage forms for a composition according to the present invention include nasal sprays and aerosols for inhalation. In a typically nasal formulation, the active ingredients are dissolved or dispersed in a suitable vehicle. The pharmaceutically acceptable vehicles and excipients and optionally other pharmaceutically acceptable materials present in the composition such as diluents, enhances, flavoring agents, preservatives, etc., are all selected in accordance with conventional pharmaceutical practice in a manner understood by the persons skilled in the art of formulating pharmaceuticals.

The pharmaceutical compositions according to the invention may also be administered topically on the skin for percutaneous absorption in dosage forms or formulations containing conventionally non-toxic pharmaceutically acceptable carriers and excipients including microspheres and liposomes. The formulations include creams, ointments, lotions, liniments, gels, hydrogels, solutions, suspensions, pastes, plasters and other kinds of transdermal drug delivery systems. The pharmaceutically acceptable carriers or excipients may include emulsifying agents, antioxidants, buffering agents, preservatives, humectants, penetration enhancers, chelating agents, gelforming agents, ointment bases, perfumes and skin protective agents.

Examples of emulsifying agents are naturally occurring gums, e.g., gum acacia or gum tragacanth, naturally occurring phosphatides, e.g., soybean lecithin and sorbitan monooleate derivatives.

Examples of antioxidants are butylated hydroxy anisole (BHA), ascorbic acid and derivatives thereof, tocopherol and derivatives thereof and cysteine.

Examples of preservatives are parabens and benzalkonium chloride.

Examples of humectants are glycerin, propylene glycol, sorbitol and urea.

Examples of penetration enhancers are propylene glycol, DMSO, triethanoiamine, N,N-dimethylacetamide, N,N-dimethylformamide, 2-pyrrolidone and derivatives thereof, tetrahydrofurfuryl alcohol and AZONE®.

Examples of chelating agents are sodium EDTA, citric acid and phosphoric acid.

Examples of gel forming agents are Carbopol, cellulose derivatives, bentonit, alginates, gelatin and PVP.

Examples of ointment bases are beeswax, paraffin, cetyl palmitate, vegetable oil, sorbitan esters of fatty acids (Span), polyethyleneglycols, and condensation products between sorbitan esters of fatty acids and ethylene oxide, e.g., polyoxyethylene sorbitan monooleate (Tween).

The formulation and preparation of the above-mentioned compositions is well-known to those skilled in the art of pharmaceutical formulation. Specific formulation can be found in "Remington's Pharmaceutical Sciences" incorporated herein by reference.

In one aspect the present invention relates to a method for treatment of overweight or obesity in individuals, in particular in humans or for reducing the adipose tissue mass/lean mass body mass ratio of an individual, in particular a human or a domestic animal.

In the present context the term "overweight" is used as an indication of a body with a weight exceeding the "desirable weight", whereas the term "obesity" is used when the body weight is 20% or more above the "desirable weight". Desirable weights for humans are given by the Council on Scientific Affairs (1) defining the desirable weights for humans according to Metropolitan Height and Weight Tables as the midpoint of the range of the medium-frame individuals.

In another aspect, the present invention relates to a method for the treatment of diseases which are complications to overweight or obesity. These diseases or conditions include diabetes mellitus type II, hypercholesterolemia, hypertriglyceridaemia and hypertension.

In another aspect, the present invention also relates to a method of reducing adipose tissue mass/lean body mass ratio or treating overweight or obesity or complications thereof by means of subjecting the individuals to a diet regimen. The diet regimen into which the individuals may be subjected in connection with the administration of the composition may include a low carbohydrate, a low fat and a low energy regimen, e.g., a diet of from 800-2500 kcal/day.

Veterinary Use

The compositions according to the invention can also be administered to domestic animals in order to improve the performance of the animal (daily weight gain and feed utilization) or to improve carcass quality or both. Carcass quality is generally improved when the fat tissue mass/lean mass body mass ratio is decreased, i.e., when the body content of meat is increased e.g., at the expense of the body content of fat.

The improvements in performance and carcass quality are suggested to be caused by a reduced fat accretion and/or by an increased skeletal muscle accretion. In growing animals, the amount of lipid present is suggested to be governed by the relative rates of lipolysis and lipogenesis. Stimulation of lipolysis and/or inhibition of lipogenesis in fat tissue may lead to a reduced fat accretion. In vivo and in vitro studies with both pigs and ruminants may indicate that certain beta agonists stimulate lipolysis and inhibit lipogenesis in fat tissue leading to a reduced fat accretion.

Administration to an animal of the compositions according to the present invention may be useful in order to increase the lean body mass at the expense of body fat, particularly in domestic animals like pigs, hogs, cattle, sheep and poultry. The composition may be given in admixture with the feed in a suitable dose corresponding to the size of the animal.

Peptide Synthesis

The peptides of the present invention, such as the extended tripeptides and their analogs (e.g. BG-116, BG-117 and BG-120), can be synthesized by any suitable method, such as by exclusively solid-phase techniques, by partial solid-phase techniques, by fragment condensation or by classical solution addition. A detailed description of these methods is contained in "The Peptides, Vol. 1", Gross and Meinenhofer, Eds., Academic Press, New York, 1979. Coupling methods employed include the carbodiimide method (1,3-dicyclohexylcarbodiimide [DCC], 1-(3-dimethylaminopropyl-3-ethylcarbodiimide hydrochloride [EDCI]) with the option of racemization preventing additives (1-hydroxybenzotriazole [HOBT]), the mixed anhydride method, the azide method, the acid chloride method, the symmetrical anhydride method, the use of bis(2-oxo-3-oxazolidinyl)phosphinic chloride (BOP-Cl), and the active ester method (N-hydroxysuccinimide esters, 4-nitrophenol esters, 2,4,5-trichlorophenol esters, and the like). Notably, the synthesis of the PYY analogs of U.S. Pat. Nos. 5,604,203, and 6,046,167 to Balasubramaniam is fully disclosed therein, which is hereby incorporated by reference herein, and further is generally discussed below. With respect to certain of the extended tripeptides, also see Pasqualini R, Ruoslahti, E. Organ targeting in vivo using phage display peptide libraries. Nature 380:364-366 (1996) and Ivanenkov VV, Menon, A G. Peptide mediated transcytosis of phage display vectors in MDCK cells. Biochem Biphys Res Communication 276:251-257 (2000).

For example, the techniques of exclusively solid-phase synthesis are set forth in the textbook "Solid-Phase Peptide Synthesis" Stewart & Young, Freeman & Co., San Francisco, 1969, and are exemplified by the disclosure of U.S. Pat. No. 4,105,603, issued Aug. 8, 1978 to Vale et al. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975). All of the above references are incorporated herein by reference.

Synthesis by the use of recombinant DNA techniques, for purposes of this application, should be understood to include the suitable employment of a structural gene coding for all of the tripeptide to transform a microorganism, using an expression vector including a promoter and operator together with such structural gene, and causing such transformed microorganism to express the peptide or such a synthetic peptide fragment. A non-human animal may also be used to produce the peptide by gene-farming using such a structural gene in the microinjection of embryos as described in U.S. Pat. No. 4,870,009 issued Sep. 26, 1989, incorporated herein by reference.

When the peptides are not prepared using recombinant DNA technology, they are preferably prepared using solid phase synthesis, such as that described by Merrifield, J. Am. Chem. Soc., 85, p 2149 (1964), although other equivalent chemical syntheses known in the art can also be used as previously mentioned. Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al., the disclosure of which is incorporated herein by reference. Such a starting material for NPY analogs can, for example, be prepared by attaching alpha-amino- and side-chain-protected Tyr to a BHA resin.

The compounds of the invention may be prepared by stepwise coupling of the amino acids or by coupling together fragments of dipeptide length or greater. Thus, the free carboxylic acid moiety from one amino acid or peptide fragment is activated and allowed to condense with the free nitrogen group of the second amino acid or peptide fragment. The coupling reactions are conducted in solvents such as methylene chloride ($CH_2Cl_2$), tetrahydrofuran (THF), dimethylformamide (DMF) or other such solvents.

During the coupling process, the non-participating carboxylic acids or amines on the reacting set of amino acids or peptide fragments are protected by a protecting group which can be selectively removed at a later time if desired. A detailed description of these groups and their selection and chemistry is contained in "The Peptides, Vol. 3", Gross and Meinenhofer, Eds., Academic Press, New York, 1981, incorporated herein in its entirety by reference. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like.

Examples of useful protective groups for the carboxylic acid include esters, such as methyl, ethyl, benzyl, t-butyl, 2,2,2-trichloroethyl, allyl, 4-nitrobenzyl, and the like. Removal of these protecting groups may be accomplished selectively by employing various acid or base catalyzed hydrolytic, hydrogenolytic, thermal or dissolving metal conditions.

Generally, peptides will be synthesized by stepwise solid phase methodology developed by using an automated Applied Biosystem Model 430A peptide synthesizer. Tertiary butyloxy-carbonyl (Boc) amino acids with benzyl or halobenzyl based side chain protecting groups (Asp & Glu with OBzl; Ser & Thr with Bzl: Cys with pMeBzl; Tyr with 2BrZ; Lys with 2ClZ; Arg with Tos; His with Bom; Trp with CHO) will be used in conjunction with phenylacetamidomethyl (PAM) resin. In the case of the synthesis of peptide amides, benzyldrylamine (BHA) or paramethylbenzylhydrylamine (MBHA) will be used instead of PAM resin.

Boc-aminoacid-PAM-resin, using Boc-aminoacyloxy-methyl-phenylacetic acid and aminomethyl resin, is available commercially. The Boc-aminoacid-PAM-resin thus prepared eliminates the possibility of chain termination by tri-fluoroacetylation. Attachment to BHA or MBHA resin will be performed by way of preformed symmetrical anhydride.

Coupling and deprotection functions are generally carried out automatically by the instrument. The standard program provided by the manufacturers are modified to incorporate a double coupling procedure, first in DMF and then in $CH_2Cl_2$. Altering the polarity of the solvents improves the coupling. All amino acids, except Asn, Gln and Arg, will generally be coupled as preformed symmetrical anhydrides. Asn, Gln and Arg are double coupled as preformed 1-hydroxy-benzotriazole esters to avoid side reactions. Resin samples taken during these reactions may be assayed by quantitative procedure to determine the degree of coupling. Other standard cleaving reagents and conditions for removal of specific alpha-amino protecting groups may be used as described in Schroder & Lubke, "The Peptides" Vol. 1, pp 72-75 (Academic Press 1965), incorporated herein in its entirety by reference.

In the case of coupling unusual amino acids, suitable conditions (solubility, coupling times) will be first developed before using in automated mode. In some cases these couplings will be carried out manually (eg: pseudopeptides, N-Me-amino acids). Pseudopeptide bonds will be incorporated by the methods described earlier. The t-Boc-amino acid aldehyde will be obtained by reducing N-methoxy-N-methylamide derivatives of Boc-amino acids with $LiAlH_4$. The aldehyde obtained will be reacted immediately with the a-amino group of the peptide attached to the resin in DMF containing 1.0% HOAC in the presence of an equivalent amount of $NaBH_3CN$. At the end of the reaction, the presence of secondary amine is tested for with ninhydrin (wine-red color). The secondary amine formed will then be blocked by reacting with 2 equivalents of Z(2-Cl)OSU, 2 equivalents of HOBT, and 4 equivalents of diisopropylethyamine until ninhydrin gives a yellow color. This way the formation of branched peptide is prevented. Coupling of sterically hindered amino acids (eg: N-Me-amino acids, $C_\alpha$MeLeu, Aib) will be effected by a HOAT or HATU which has been shown to be superior to BOP/HOBT.

For the final cleavage, the N-α-Boc group and the Nin-CHO will be first removed with 50% TFA/$CH_2Cl_2$ and 20% piperidine-DMF from the protected peptide resin before detaching the target peptide using HF containing p. cresol (5%). If Cys and Met are present, p. thicresol (2.5%) will also be added to the HF reaction mixture. If problems are encountered during the standard HF method, then the "low/high" HF procedure will be used.

The materials are then purified. After initial fractionation on Sephadex G-25, the peptide material will be subjected to reversed phase high performance liquid chromatography (RPLC) on $C_{18}$ Vydac columns. However, peptides may be first subjected to ion exchange chromatography before RPLC, depending upon the heterogeneity of the crude peptide. The homogeneity of the purified product may be confirmed by analytical RPLC using two different solvent systems, amino acid analysis, complete sequencing, and mass spectral analysis.

For analysis, the peptide resins are hydrolyxed using 12N HCl/HOAc/phenol (2:1:1) for 24 hours at 11° C. The free peptides are hydrolyzed for 24 hours in 6N HCl containing 0.1% phenol or 4N methane sulfonic acid at 110° C. and are quantified on a Waters Pico Tag system. Peptide hormones and fragments are then subjected to complete sequencing on an automated gas phase sequencer (Applied Biosystem, Model 470A).

For the production of a compound of the invention where any one or several of the constituent amino acids bear an N-alkyl group, specifically methyl, the corresponding N-alkyl amino acid can be prepared via the method described by Benoiton (*Can. J. Chem.*, 1977, 55:906) or Shuman ("Peptides: Proceedings of the 7th American Peptide Symposium", D. Rich, E. Gross, Eds., Pierce Chemical Co., Rockford, Ill. 1981, p 617), wherein the t-BOC- or Cbz-protected amino acid is treated with a base in the presence of a chelating agent such as a crown ether and then quenched with methyl iodide. An alternative method described by Freidinger (*J. Org. Chem.*, 1983, 48:77), in which triethylsilane reduction of the oxazolidinone of an amino acid directly produces the N-methyl derivative may also be utilized.

The reduced carbonyl amide bond surrogates can be prepared in a manner similar to that described by Martinez (*J. Med. Chem.* 1987, 30:1366). The N-alpha-t-BOC protected amino acid (with appropriate protection of side chain functional groups) is converted to the 3,5-dimethylpyrazolide, which is then reduced with lithium aluminum hydride. The resulting aldehyde is then allowed to condense with an amino acid or peptide bearing a free amino terminus. Reduction of the Schiff base which is formed as a result of the condensation is accomplished using sodium cyanoborohydride to yield the desired compound having a reduced amide bond.

Functionalization of the epsilon-amino group of the lysine (Lys) or homologous (e.g., Orn) residue is achieved via activation of the acid fragment as the active ester (N-hydroxysuccinimide, 2,4,5-trichlorophenol, etc.) or, if no other free carboxylic acid function is present on the peptide, coupling using any of the methods mentioned above is applicable. In addition, the functionalization of the epsilon-amino group may be accomplished by reaction with various alkyl and aryl isocyanates, as well as alkyl and aryl isothiocyanates.

The sulfuric acid esterification of the phenolic residues may be conducted using a variety of known reagents such as the pyridine-sulfuric anhydride or the pyridine-sulfur trioxide complex. Use of pyridinium acetyl sulfate as described by Penke and Rivier ("Proceedings of the 8th American Peptide Symposium", V. Hruby, D. Rich, Eds., Pierce Chemical Company, Rockford, Ill.; 1983; p. 119), may also be applied to prepare the sulfuric acid ester derivative of the tetrapeptides.

The O-glycosylated tripeptides, i.e. the O-glycopeptides, and their analogs of the present invention generally may be synthesized as described by Gangadhar et al. (*Tetrahedron Letters*, 2004, 45:355-358), incorporated herein by reference, wherein Fmoc-AA-OPfp (AA=Tyr or Ser) (1 equiv) is reacted with gylcosylpentaacetate, $\beta$-D-Glc(OAc)$_5$, (6 equiv) in the presence of glycosylating agents such as $BF_3.Et_2O$ (6 equiv) in $CH_2Cl_2$ at room temperature for 2 hours. The resulting glycosylation mixture, Fmoc-AA-[$\beta$-D-Glc(OAc)$_4$] OPfp, is used directly to couple to an amino acid group of a peptide resin, via a peptide synthesizer, without isolation and purification of the glycosylation mixture. The OAc protecting groups of the monosaccharide, e.g. glucose, may be removed just prior to releasing the peptide form the resin using 6 mM NaOMe in 85% DMF-MeOH. Advantageously, the tripeptides and their analogs as disclosed in U.S. Pat. Nos. 6,013,633 and 6,235,718 to Balasubramanium et al., incorporated herein by reference, may be O-glycosylated according to the aforementioned procedure. Most preferably, the tripeptide analog, N-$\alpha$-Ac-Trp-Arg-NH$_2$ (BT-54), may be O-glycosylated, as further specifically described below, to produce the novel compound N-$\alpha$-Ac-Trp-Arg-Tyr-[$\beta$-D-Glc]-NH$_2$ (BG-7) which can inhibit feeding in subjects. In addition, while AA is indicated as being Tyr or Ser, any aromatic hydroxy amino acid may be utilized such as Thr and derivatives thereof, N-Me-Tyr, C$_\alpha$Me-Tyr, Tic-OH, descarboxylic tyrosine (tyramine), etc.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

The pharmaceutically acceptable salts of the present invention can be synthesized which contain a basic or acidic moiety by conventional chemical methods. Generally, the salts are prepared by reacting the free base or acid with stoichiometric amounts or with an excess of the desired salt forming inorganic or organic acid or base in a suitable solvent or various combinations of solvents.

Examples of preferred salts are those with therapeutically acceptable organic acids, e.g., acetic, lactic, maleic, citric, malic, ascorbic, succinic, benzoic, or pamoic acid, as wells as polymeric acids and salts with inorganic acids such as the hydrohalic acids, e.g., hydrochloric and sulfuric acids.

In addition, pseudopeptide bonds may, if desired, be introduced at various positions, e.g., between amino acid residues A1-A2 or between residues A2-A3. Optically pure Boc-AA-CHO can be obtained in good yields and coupled directly to the —NH2 group of the peptide resin by published methods (Sasaki et al., Peptides 8:119-121, 1987; Fehrentz et al., *Synthesis* pp. 676-678, 1983). The secondary amine in the pseudopeptide bond is capped with Z(2-CI). This is introduced by reacting the peptide resin with Z(2-CI)-OSU (2 equiv.), HOBT (2 equiv.) and DIEA (4 equiv.) for 10-60 min.

The red wine color of ninhydrin with secondary amine turns yellow at the end of capping. Exemplary compounds of the present invention include:

```
1. N-α-Ac-Trp-Arg-Tyr-[β-D-Glc]-NH₂

2. N-α-Ac-Trp-Arg-Tyr-[β-D-Glc(OAc)₄]-NH₂

3. H-Ser(β-D-Glc)-Gly-Ala-NH₂

4. H-Ser[β-D-Glc(OAc)₄]-Gly-Ala-NH₂

5. H-Tyr(β-D-Glc)-Gly-Ala-NH₂

6. H-Tyr(β-D-Lac)-Gly-Ala-NH₂

7. H-Tyr[β-D-Glc(OAc)₄]-Gly-Ala-NH₂

8. H-Tyr-Gly-Arg-Lys-Lys-Arg-Arg-Gln-Arg-Arg-
   NH—CH₂—CH₂—CO-Trp-Arg-Tyr-NH₂
   (SEQ. ID. NO. 12)

9. H-Tyr-Gly-Arg-Lys-Lys-Arg-Arg-Gln-Arg-Arg-
   NH—CH₂—CH₂—CO-[Trp-Arg-Tyr]₂-NH₂
   (SEQ. ID. NO. 13)

10. H-Tyr-Gly-Arg-Lys-Lys-Arg-Arg-Gln-Arg-Arg-
    O—CH₂—CO-Trp-Arg-Tyr-NH₂
    (SEQ. ID. NO. 14)

11. N-α-Ac-[Trp²⁷, ψ³⁵/³⁶]PYY(25-36)-NH₂, wherein ψ
    is —CH2—NH—
    (SEQ. ID. NO. 7)

12. N-α-Ac-[Trp³⁰]PYY(25-36)-NH₂, wherein ψ is
    —CH2—NH—
    (SEQ. ID. NO. 6)

13. N-α-Ac[Nle²⁴,²⁸, Trp³⁰, Nva³¹, ψ³⁵/³⁶]PYY
    (22-36)-NH₂, wherein ψ is —CH2—NH—
    (SEQ. ID. NO. 8)

14. H-[Tyr(β-D-Glc)]-NH—CH₂—CH₂—CO-Trp-Arg-Tyr-HN₂
    (SEQ. ID. NO. 12)

15. H-Cys-Leu-Ser-Ser-Arg-Leu-Asp-Ala-Cys-
    NH—CH₂—CH₂—CO-Trp-Arg-Tyr-HN₂
    (SEQ. ID. NO. 16)

16. Ac-Arg-Tyr-Arg-Gly-Asp-Leu-Gly-Leu-Gly-Arg-Arg-
    NH—CH₂—CH2—CO-Trp-Arg-Tyr-HN₂
    (SEQ. ID. NO. 17)

17. Ac-Cys-Arg-Tyr-Arg-Gly-Asp-Leu-Gly-Leu-Gly-Arg-
    Arg-Cys-NH—CH₂—CH₂—CO-Trp-Arg-Tyr-HN₂.
    (SEQ. ID. NO. 18)
```

Other analogs of the invention can be prepared as above and tested for their biological activity effectiveness as antagonists or agonists using the methods described below and those commonly known in the art.

Functional Assays

Animals. Cell Lines and Cultures. and Reagents

Any suitable in vivo or in vitro system may be utilized to assay and test the effectiveness of the compounds of the invention. Such assays may employ in vivo methods for evaluating physiological responses, e.g., blood pressure, renovascular function, feeding behavior, or circadian rhythm, or in vivo biochemical systems evaluating receptor binding in a suitable cell line, e.g., SK-N-MC (ATCC HBT 10) or SK-N-BE(2) (Barnes et al. In Vitro, 17: 619 631, 1981); or in isolated cells, e.g., cells isolated from the spleen, kidney, heart or brain. A number of in vivo and in vitro biochemical systems known to those skilled in the art are available for testing antagonists to hypothalamic NPY receptors, e.g. the Y-1, Y-2, and Y-3 receptor categories. Described below are assay methods which can be utilized with cell lines such as SK-N-MC and SK-N-BE2 or isolated cardiac membranes which possess the high-affinity hypothalamic NPY receptor sites. Other systems are also known for evaluating NPY antagonists to the hypothalamic NPY receptor, e.g. VSM cells (Sheikh et al, Am. *J. Physiol.* 260: G250 G257, 1991) and HEL cells (Motulsky et al. Amer. J. *Physiol.* 255: E880-E885, 1988); Y-2 receptor, e.g., kidney (Sheikh et al., Am. J. *Physiol* 26:F978-F984), spleen (Lunberg et al., Eur. J. Pharmal. 145:21-29, 1988), dorsal root ganglion (Bleakman et al., Br. J. Pharmal. 103:1781-1789, 1991) and hippocampal cells (Sheikh et al., J. Biol. Chem. 265:8304 8310, 1990); and Y-3 receptors, e.g., in cardiac ventricular membranes (Balasubramaniam et al., Peptides 11: 545-550, 1990), chromaffin cells, rat gastric mucosa (Michel, M. C., *Trends in Pharmol. Sci.* 12: 389-394, 1991) and brain stem.

In Vitro Biochemical Assays

The ability of the compounds of the invention to act as antagonists of NPY can be demonstrated by any number of methods known in the art. For example, the compounds can be shown to compete with iodinated neuropeptide Y for receptors using the methods described by Lundberg et al. (*Eur. J. Pharmol.* 145: 21-29, 1988); Gordon et al. (*J. Neurochemistry* 55:506-513, 1990); Walker et al. (*Mol. Pharmacol.* 34:779 792, 1988); Balasubramaniam et al. (*Peptides* 10:1283-1286, 1989).

In one example demonstrating antagonists to hypothalamic NPY receptors, rat hypothalmus was isolated and the membranes were prepared for binding and adenylate cyclase studies according to standard methods (Unden et al. 1984. *Eur. J. Biochem* 145: 525-530; Westlind-Danielsson et al., *Neurosci. Lett.* 74: 237-242 (1987)). Displacement studies are performed in a total volume of 0.25 ml 20 mM HEPES buffer, pH 7.4, containing 1% bovine serum albumin, 0.1% bacitracin, 300 μm PMSF and 5 KIU/ml aprotinin. In a standard assay, 100 μg of membrane/tube is incubated in a shaking water bath at 24° C. for 45 min with [$^{125}$I-Tyr]-NPY (20,000 CPM) as described by Balasubramaniam et al., (*Peptides* 11: 545-550, 1990), in the presence of increasing concentrations of NPY (10 μOsM). At the end of incubation, 1.0 ml of iced cold buffer is added, centrifuged at 10,000×g for 10 min, and the supernatant removed by aspiration. The tube containing the pellet is counted for bound radioactivity in a micromedic gamma counter.

An example of assaying adenylate cyclase activity of hypothalamic and cerebral cortex membranes is now described.

Adenylate cyclase activity of the hypothalamic and cerebral cortex membranes is determined by incubating 50 μg of membranes in a total volume of 0.20 ml Tris-HCμ 30 mM pH 7.4 buffer containing 150 mM NaCl, 8.25 mM MgCl2, 0.75 mM EGTA, 1.5 theophylline, 20 μg/ml aprotinin, 100 μg/ml bacitracin, 1 mg/ml bovine serume albumin, 1 mM ATP, 20 mM creatine phosphate, 1 mg/ml phosphocreatine kinase, 10 μM isopretemol, 10 μM GTP, and various concentrations of peptides (0-10 μM). After incubating the mixture at 35° C. for 15 min in a shaking water bath, the reaction is arrested by the addition of 100 μM EDTA and boiling for 3 min. cAMP is extracted and quantitated by radioimmunoassay. All the points in the binding and adenlyate cyclase are the means of at least three parallel experiments performed in duplicate.

In Vivo Assays

Any suitable in vivo model system can be used to evaluate the antagonistic properties of the compounds of the invention. Such models, without limitation, include those used to evaluate feeding and memory behavior (Flood et al., *Peptides*

10:963-966), and vasoconstiction and hypertension (Balasubramaniam et al. *Biochem et Biophys Acta* 997: 176-188, (1989)).

Thus, in one example, feeding studies are performed using Spraque Dawley rats (350-450 g) with paraventricular hypothalmic cannulae to investigate effects of NPY analogs (Chance et al., *Peptides* 10: 1283, 1286 (1989)).

The following Examples set forth preferred methods for synthesizing tripeptides, such as the extended tripeptides of the present invention, by the solid-phase technique and generally is in accordance with the procedure set forth in U.S. Pat. No. 4,415,558 to Vale, et al., issued Nov. 15, 1983, the disclosure of which is incorporated herein by reference.

Additional Examples further set forth preferred methods for synthesizing O-glycosylated tripeptides by the technique generally in accordance with the procedure set forth in Gangadhar et al. (*Tetrahedron Letters*, 2004, 45:355-358), the disclosure of which is incorporated herein by reference.

EXAMPLES

Example I

The extended tripeptide H-Tyr-Gly-Arg-Lys-Lys-Arg-Arg-Gln-Arg-Arg-Arg-β-Ala-Trp-Arg-Tyr-NH$_2$(BG-116) (SEQ. ID. NO. 12) is synthesized in a stepwise manner, i.e. amino acid by amino acid in a direction from tripeptide moiety to linker to TAT peptide moiety, on a methylbenzhydrylamine hydrochloride resin, such as available from Bachem, Inc., having a substitution range of about 0.1 to 0.5 mmoles/g resin. The synthesis is performed on an automatic Applied Biosystems, Model 430A, peptide synthesizer using the program supplied by the manufacturer. The amino acids are coupled using 4.4 equivalents of preformed 1-hydroxybenzotriazole esters. At the end of the synthesis, the TAT alpha-amino group is hydrogenated and the extended tripeptide detached, purified, and characterized.

Example II

To study the feeding patterns of animals treated with the extended tripeptide BG-116, eight week old 129/J male mice are individually housed under 12-hour light/dark cycles with free access to water and standard chow. After acclimatizing for two weeks, mice are fasted 24 hours before the experiment. Saline (0.1 ml) or peptide (2 mg/mice) in saline (0.1 ml) is injected intraperitoneally, and the food intake during the next 4, 6, and 24 hours is monitored and quantified. The results are shown in FIG. 1.

Example III

The O-glycosylation of the tripeptide N-α-Ac-Try-Arg-Tyr-NH$_2$ (BT-54) to produce N-α-Ac-Trp-Arg-Tyr-[β-D-Glc]-NH$_2$ (BG-7) is conducted as follows:

Synthesis of N$^\alpha$-Fmoc-Tyr[β-D-Glc(OAc)$_4$]-OPfp: Fmoc-Tyr-OPfp (0.5 mmol, 1 equiv), β-D-Glc(OAc)$_5$ (1.17 g, 3 mmol, 6 equiv) and CH$_2$Cl$_2$ (10 ml) is placed in a round bottom flask and N$_2$ gas is bubbled for 5 min. BF$_3$.Et$_2$O (390 µl, 3 mmol, 6 equiv) is then added and N$_2$ gas bubbling continued for another 5 min. The flask is stoppered and stirred for 2 hr at room temp. Completion of the reaction is checked by TLC. (TLC plates are developed with ethylacetate-petroleum ether (1:2) and the amino acid spots are visualized using UV light. R$_f$, 0.64 (Fmoc-Tyr-OPfp), 0.35 {Fmoc-Tyr[Glc (OAc)$_4$]-OPfp}). The reaction mixture is then diluted with CH$_2$Cl$_2$ (40 ml), washed with water (2×20 ml), dried over anhydrous Na$_2$SO$_4$, evaporated and the residues are dissolved in DMF (10 ml) and used in the next step without further purification.

Solid Phase synthesis of the O-glycosylated tripeptide: N-α-Fmoc-Tyr[β-D-Glc(OAc)$_4$]-OPfp (2 equvi) generated as described above is manually coupled to NH$_2$-Knorr-MBHA RESIN in the presence of HOBT (2 equivi) and disisopropyl amine (4 equivi) in a round bottom flask. When the reaction is completed as judged by ninhydrin test, the N-α-Fmoc-Tyr[β-D-Glc(OAc)$_4$]-NH-Knorr-MBHA-RESIN is introduced into the reaction vessel of an ABI 431A peptide synthesizer, and the protected amino acids are sequentially coupled using the program provided by the manufacturers. At the end of the synthesis N-α-Fmoc group is removed automatically and the α-amino group is acylated with Ac$_2$O. Then the OAc-protecting group of the glucose is removed with 6 mM NaOMe in 85% DMF-MeOH, and free peptide obtained the treating peptide resin with Reagent K, which is trifluoroacetic acid (TFA) containing 5% thioanisole, 5% phenol, 5% water & 2.5% ethanedithiol.

Example IV

Figure 2:
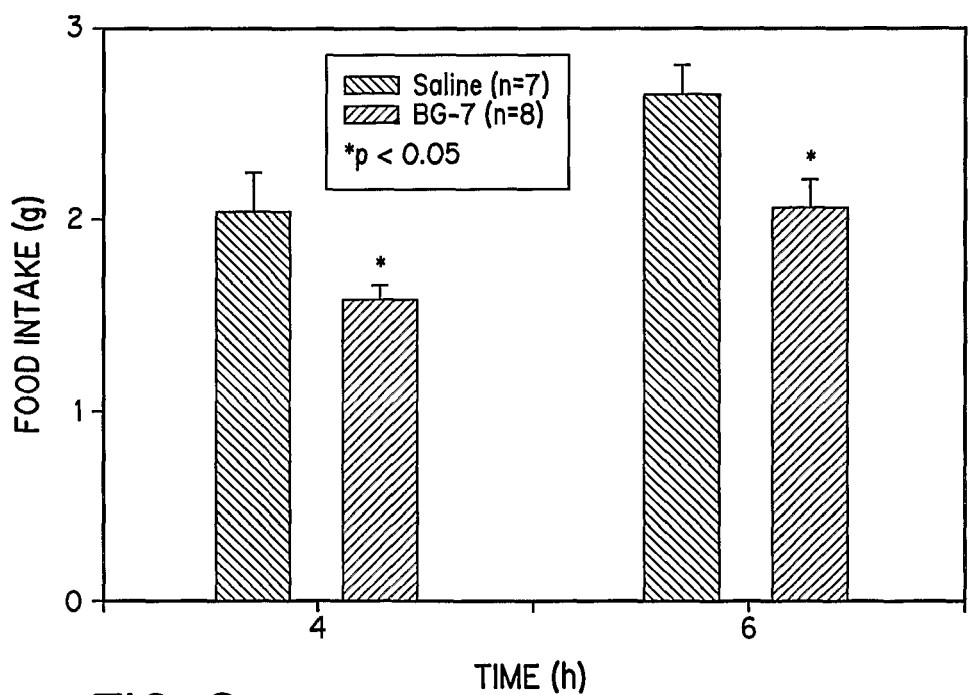
FIG. 2. A graph representing the feeding patterns of animals treated with an O-glycosylated tripeptide by intraperitoneal injection. The compounds tested include control (saline) and BG-7 (N-α-Ac-Trp-Arg-Tyr-[β-D-Glc]-$NH_2$).

To study the feeding patterns of animals treated with the O-glycosylated tripeptide, eight week old 129/J male mice are individually housed under 12-hour light/dark cycles with free access to water and standard chow. After acclimatizing for two weeks, mice are fasted 24 hours before the experiment. Saline (0.1 ml) or peptide (2 mg/mice) in saline (0.1 ml) is injected intraperitoneally, and the food intake during the next 4 and 6 hours is monitored and quantified. The results are shown in FIG. 2.

The following PYY analogs, in Examples V-VII, were studied and unexpectedly yielded results indicating that they could be used to control food intake in animals and humans. Accordingly, PYY(22-36) and PYY(25-36), and their deletion peptides, as disclosed in U.S. Pat. Nos. 5,604,203, and 6,046,167 to Balasubramaniam, are expected to prove useful in at least controlling appetite and the treatment of weight problems (e.g. obesity, diabetes), eating disorders, and such.

Example V

Figure 3:
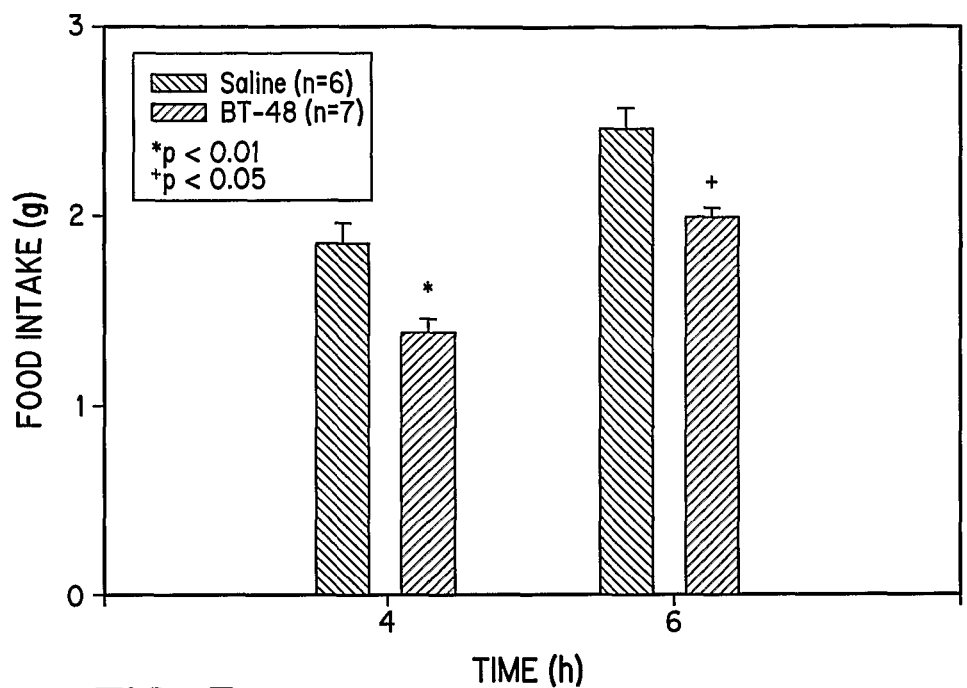
FIG. 3. A graph representing the feeding patterns of animals treated with a PYY analog by intraperitoneal injection. The compounds tested include control (saline) and N-α-Ac[$Nle^{24,28}$, $Trp^{30}$, $Nva^{31}$, $\psi^{35/36}$]PYY(22-36)-$NH_2$ (BT-48) (SEQ. ID. NO. 8) wherein ψ is —$CH_2$—NH—.

To study the feeding patterns of animals treated with BT-48 or N-α-Ac[Nle$^{24,28}$, Trp$^{30}$, Nva$^{31}$, ψ$^{35/36}$]PYY(22-36)-NH$_2$ wherein ψ is —CH2-NH— (SEQ. ID. NO. 8), eight week old 129/J male mice are individually housed under 12-hour light/dark cycles with free access to water and standard chow. After acclimatizing for two weeks, mice are fasted 24 hours before the experiment. Saline (0.1 ml) or peptide (100 µg/mice) in saline (0.1 ml) is injected intraperitoneally, and the food intake during the next 4 and 6 hours is monitored and quantified. The results are shown in FIG. 3.

Example VI

Figure 4:
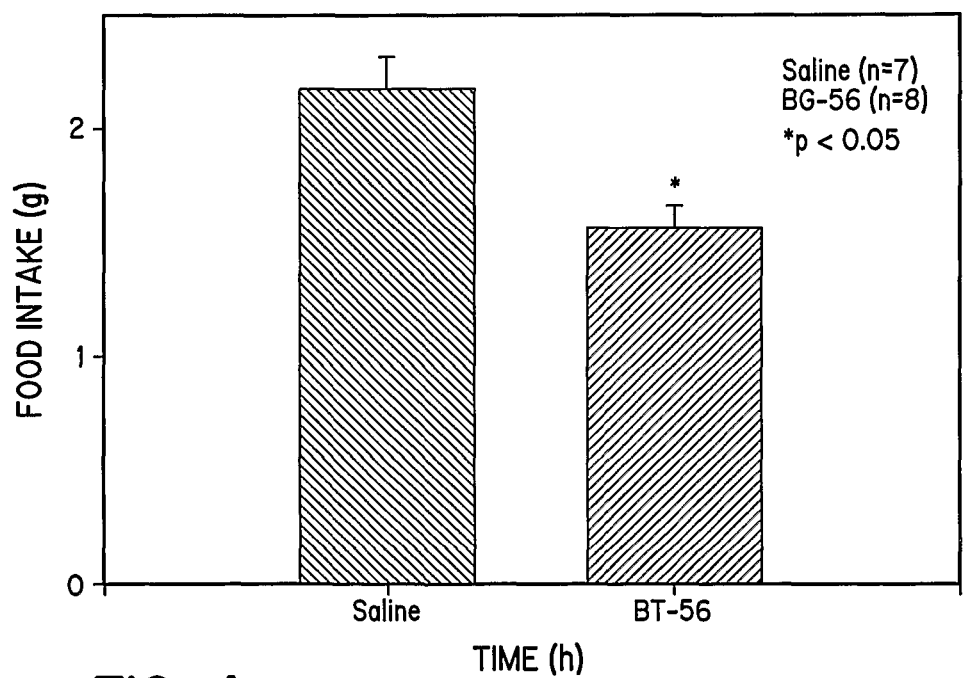
FIG. 4. A graph representing the feeding patterns of animals treated with a PYY analog by intraperitoneal injection. The compounds tested include control (saline) and N-α-Ac-[$Trp^{27}$, $\psi^{35/36}$]PYY(25-36)-$NH_2$ (BT-56) (SEQ. ID. NO. 7) wherein ω is —CH2-NH—.

To study the feeding patterns of animals treated with the BT-56 or N-α-Ac-[Trp$^{27}$, ψ$^{35/36}$]PYY(25-36)-NH$_2$ wherein ψ is —CH2-NH— (SEQ. ID. NO. 7), eight week old 129/J male mice are individually housed under 12-hour light/dark cycles with free access to water and standard chow. After acclimatizing for two weeks, mice are fasted 24 hours before the experiment. Saline (0.1 ml) or peptide (100 µg/mice) in saline (0.1 ml) is injected intraperitoneally, and the food intake during the next 4 hours is monitored and quantified. The results are shown in FIG. 4.

Example VII

Figure 5:
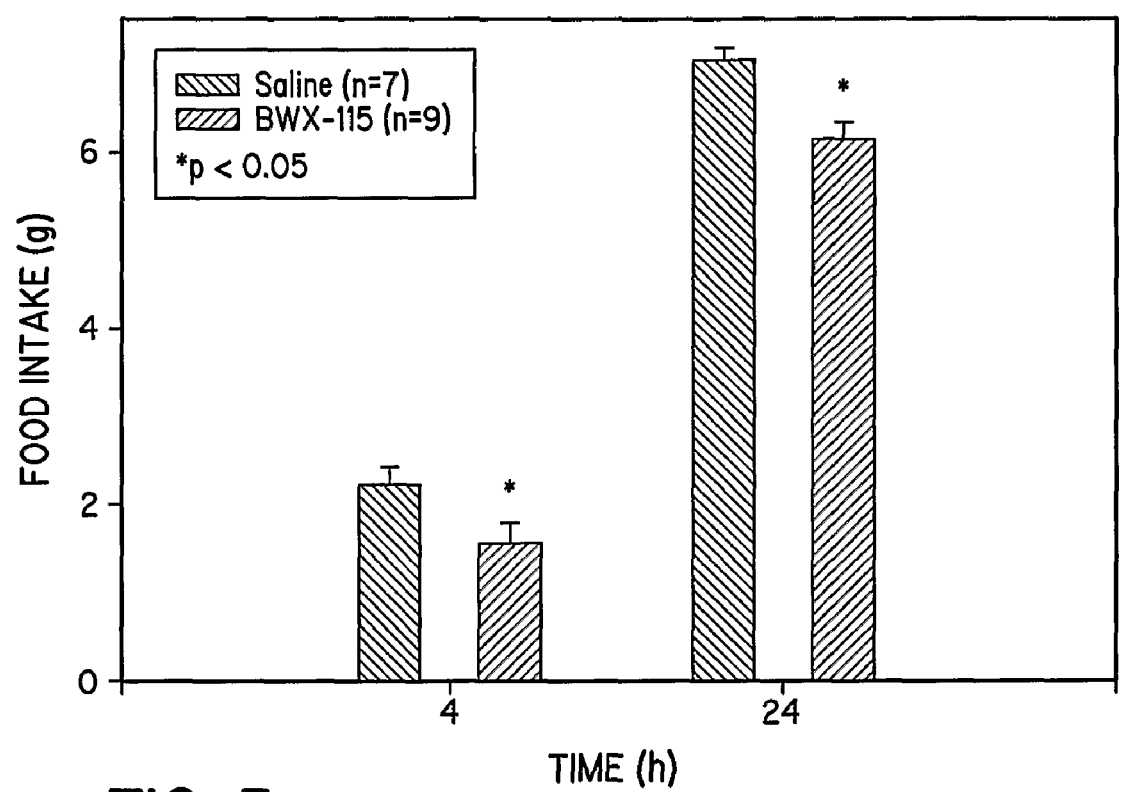
FIG. 5. A graph representing the feeding patterns of animals treated with a PYY analog by intraperitoneal injection. The compounds tested include control (saline) and N-α-Ac-[$Trp^{30}$]PYY(25-36)-$NH_2$ (BWX-115) (SEQ. ID. NO. 6) wherein ψ is —CH2-NH—.

To study the feeding patterns of animals treated with BWX-115 or N-α-Ac-[Trp$^{30}$]PYY(25-36)-NH$_2$ wherein ψ is —CH2-NH— (SEQ. ID. NO. 6), eight week old 129/J male mice are individually housed under 12-hour light/dark cycles with free access to water and standard chow. After acclimatizing for two weeks, mice are fasted 24 hours before the experiment. Saline (0.1 ml) or peptide (20 μg/mice) in saline (0.1 ml) is injected intraperitoneally, and the food intake during the next 4 and 24 hours is monitored and quantified. The results are shown in FIG. 5.

While the present invention has been illustrated by the description of the various embodiments thereof, and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope of Applicants' general inventive concept. Various features of the invention are emphasized in the claims which follow.

---

What is claimed is:

1. A method for controlling an NPY mediated physiological response in a subject comprising administering to said subject a compound having the formula:

R8-linker[A1-A2-A3]$_n$-W wherein:

R8 is H-Tyr-Gly-Arg-Lys-Lys-Arg-Arg-Gln-Arg-Arg-Arg-(SEQ. ID. NO.1), H-[X(Y)]$_n$-where X is Ser, Thr, or Tyr, Y is β-D-Glc or β-D-Gal, and n is 1, 2, or 3,

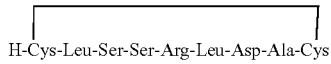
H-Cys-Leu-Ser-Ser-Arg-Leu-Asp-Ala-Cys (SEQ. ID. NO. 9), Ac-Arg-Tyr-Arg-Gly-Asp-Leu-Gly-Leu-Gly-Arg-Arg (SEQ. ID. NO. 10), or

Ac-Cys-Arg-Tyr-Arg-Gly-Asp-Leu-Gly-Leu-Gly-Arg-Arg-Cys

SEQ. ID. NO. 11);

A1 is a D or L-amino acid selected from Cys, Leu, Dap, Trp, Gln, a tethered amino acid with an indole ring, Phe, Hyp, a Trp derivative; C$_\alpha$Me-Trp, C$_\alpha$Me-Gln, Desamino-Trp, Pyr, Bth, Nal, Tcc, Asn, Nva, Abu, Ser, Tyr, Tic-OH, Phe, Tip, and Dip;

Linker is a compound that forms a peptide bond with A1 and forms one of either a peptide or ester bond with R8;

A2 is a D or L-amino acid selected from Gly, Cys, Trp, Arg, N-Me-Arg, C$_\alpha$Me-Arg, Orn, Cit, hArg(R)2 where R is selected from hydrogen, alkyl, aryl, aralkyl, or alkylaryl, Lys-ε-NH-R where R is selected from hydrogen, alkyl, aryl, aralkyl, or alkylaryl;

A3 is a D or L-amino acid selected from Glu, Tyr, N-Me-Tyr, C$_\alpha$Me-Tyr, Tic-OH, Tic, Dip, Trp, Phe, des-carboxylic-Tyr, and Tyr-(R) where R is hydrogen or a lipophilic group;

n=1, 2 or 3

W is —OH, —N-R3R4, or OR5 where R3, R4, and R5, independently, is H, C1-C12 alkyl, C6-C18 aryl, C1-C12 acyl, C7-C18 aralkyl, or C7-C18 alkaryl; or a pharmaceutically acceptable salt thereof; and each bond between two amino acids or amino acid derivatives, represented by a dash ("-"), can be either a peptide bond or a pseudopeptide bond; or a pharmaceutically acceptable salt thereof.

2. The method of claim 1, wherein the compound is H-Tyr-Gly-Arg-Lys-Lys-Arg-Arg-Gln-Arg-Arg-Arg-NH—CH$_2$—CH$_2$—CO-Trp-Arg-Tyr-N H$_2$ (SEQ. ID. NO. 12).

3. The method of claim 1, wherein administering to said subject comprises administering to said subject the compound together with a pharmaceutically acceptable carrier substance, which defines a therapeutic composition, in a therapeutically effective amount to control the NPY mediated physiological response.

4. The method of claim 3, wherein the composition is capable of suppressing appetite.

5. The method of claim 3, wherein the composition is in the form of a pill, tablet, or capsule for oral administration to a subject.

6. The method of claim 3, wherein the composition is in the form of a liquid for oral administration to a subject.

7. The method of claim 3, wherein the composition is in the form of a liquid for nasal administration as drops or spray to a subject.

8. The method of claim 3, wherein the composition is in the form of a liquid for intravenous, subcutaneous, parenteral, or intraperitoneal administration to a subject.

9. The method of claim 3, wherein the composition is in the form of a biodegradable sustained-release composition for intramuscular administration to a subject.

10. The method of claim 3, wherein the composition includes a lipophilic salt and is suitable for administration in the form of an oil emulsion or dispersion to a subject.

11. The method of claim 1, wherein the compound defines a pharmaceutically acceptable salt.

* * * * *

UNITED STATES PATENT AND TRADEMARK OFFICE
CERTIFICATE OF CORRECTION

PATENT NO. : 7,994,119 B2
APPLICATION NO. : 11/658061
DATED : August 9, 2011
INVENTOR(S) : Ambikaipakan Balasubramaniam It is certified that error appears in the above-identified patent and that said Letters Patent is hereby corrected as shown below:

On the Title Page: Item (56) References Cited

Column 1,
Line approx. 43, "Balasubramanium" should be --Balasubramaniam--.
Line approx. 44, "Balasubramanium" should be --Balasubramaniam--.
Line approx. 56, "develpment: prespective" should be --development: perspective--.

In the Specifications:

Column 1,
Line 51, "actions other drugs" should be --actions of other drugs--.

Column 2,
Line 22, "has" should be --have--.

Column 5,
Lines 53-54, "Balasumbramaniam" should be --Balasubramaniam--.

Column 6,
Line 6, "YYY" should be --PYY--.

Column 7,
Line 23, "acetylyated or nonacetylyated" should be --acetylated or nonacetylated--.
Line 24, "acetylyated or nonacetylyated" should be --acetylated or nonacetylated--.
Line 27, "OR5 (where" should be --OR5, where--.
Line 28, "is" should be --are--.
Lines 56-57, "anacetylyated or nonacetylyated" should be --an acetylated or nonacetylated--.
Line 58, "nonacetylyated" should be --nonacetylated--.

Signed and Sealed this
Eighteenth Day of September, 2012

David J. Kappos
*Director of the United States Patent and Trademark Office*

CERTIFICATE OF CORRECTION (continued)
U.S. Pat. No. 7,994,119 B2

Column 8,
Line 40, "OR5 (where" should be --OR5, where--.
Line 41, "is" should be --are--.

Column 9,
Line 29, "acids" should be --acid--.

Column 12,
Line 30, "CH2" should be --$CH_2$--.
Line 35, "CH2" should be --$CH_2$--.

Column 13,
Line 24, "acetylyated or nonacetylyated" should be --acetylated or nonacetylated--.
Line 25, "nonacetylyated" should be --nonacetylated--.
Line 28, "OR5 (where" should be --OR5, where--.
Line 29, "is" should be --are--.
Lines 53-54, "acetylyated or nonacetylyated" should be --acetylated or nonacetylated--.
Line 55, "nonacetylyated" should be --nonacetylated--.

Column 14,
Line 48, "OR5 (where" should be --OR5, where--.
Line 49, "is" should be --are--.

Column 18,
Line 16, "form a pill" should be --form of a pill--.
Line 33, "symbol" should be --symbols--.
Line 34, "stands" should be --stand--.

Column 19,
Line 61, "terms" should be --term--.
Line 61, "refer" should be --refers--.

Column 21,
Line 1, "dissaccharide" should be --disaccharide--.
Lines 49-50, "administer a particular compounds" should be --administer particular compounds--.

Column 22,
Line 19, "provide" should be --provides--.
Line 26, "anhydrides" should be --anhydride--.

Column 23,
Line 17, "enhances" should be --enhancers--.

Column 26,
Line 26, "are" should be --is--.
Line 54, "diisopropylethyamine" should be --diisopropylethylamine--.

Column 27,
Line 11, "hydrolyxed" should be --hydrolyzed--.

Column 28,
Line 7, "form" should be --from--.
Line 10, "Balasubramanium" should be --Balasubramaniam--.
Line 54, "as wells as" should be --as well as--.
Line 60, "A1-A2or between" should be --A1-A2 or between--.

Column 29,
Line 27, "CH2" should be --$CH_2$--.
Line 31, "CH2" should be --$CH_2$--.
Line approx. 34, "CH2" should be --$CH_2$--.
Line approx. 42, "CH2" should be --$CH_2$--.

Column 30,
Line 49, "adenlyate" should be --adenylate--.
Line 61, "adenlyate" should be --adenylate--.

Column 34,
Line 11, "Applicants'" should be --Applicant's--.

In the Claims:

Column 43,
Claim 1, Line approx. 6, "R8-linker[A1-A2-A3]$_n$-W" should be --R8-linker-[A1-A2-A3]$_n$-W--.

Column 44,
Claim 1, Line 3, "is" should be --are--.